(12) United States Patent
Zipprich

(10) Patent No.: US 9,308,061 B2
(45) Date of Patent: Apr. 12, 2016

(54) DENTAL IMPLANT

(76) Inventor: Holger Zipprich, Darmstadt (DE)

(*) Notice: Subject to any disclaimer, the term of this patent is extended or adjusted under 35 U.S.C. 154(b) by 0 days.

(21) Appl. No.: 13/125,105

(22) PCT Filed: Oct. 28, 2009

(86) PCT No.: PCT/EP2009/007702
§ 371 (c)(1),
(2), (4) Date: May 11, 2011

(87) PCT Pub. No.: WO2010/049135
PCT Pub. Date: May 6, 2010

(65) Prior Publication Data
US 2011/0223562 A1      Sep. 15, 2011

(30) Foreign Application Priority Data
Oct. 31, 2008   (DE) .......................... 10 2008 054 138

(51) Int. Cl.
*A61C 8/00*      (2006.01)
(52) U.S. Cl.
CPC ............... *A61C 8/005* (2013.01); *A61C 8/0066* (2013.01)
(58) Field of Classification Search
CPC ........................................... A61C 8/00–8/0098
USPC ................................................. 433/172–176
See application file for complete search history.

(56) References Cited

U.S. PATENT DOCUMENTS

| | | | |
|---|---|---|---|
| 3,110,626 A | 11/1963 | Larson et al. | |
| 4,335,676 A | 6/1982 | Debayeux et al. | |
| 4,713,003 A * | 12/1987 | Symington et al. | 433/173 |
| 5,195,892 A * | 3/1993 | Gersberg | 433/174 |
| 5,246,370 A * | 9/1993 | Coatoam | 433/173 |
| 5,437,551 A | 8/1995 | Chalifoux | |
| 5,782,918 A * | 7/1998 | Klardie et al. | 606/60 |
| 6,244,867 B1 * | 6/2001 | Aravena et al. | 433/172 |
| 6,419,492 B1 * | 7/2002 | Schroering | 433/173 |
| 6,537,069 B1 | 3/2003 | Simmons, Jr. | |
| 6,648,643 B2 * | 11/2003 | Hollander et al. | 433/173 |
| 7,014,464 B2 * | 3/2006 | Niznick | 433/173 |
| 7,056,117 B2 | 6/2006 | Simmons, Jr. | |

(Continued)

FOREIGN PATENT DOCUMENTS

DE            19753577 A1       6/1999
DE         102006018726 A1     10/2007

(Continued)

OTHER PUBLICATIONS

English language translation of WO2007/121939, Nov. 1, 2007.*

(Continued)

*Primary Examiner* — Edward Moran
(74) *Attorney, Agent, or Firm* — Suzannah K. Sundby, Esq.; Canady + Lortz LLP

(57) ABSTRACT

Disclosed herein is a dental implant (1) having a post part (2) which can be placed in a jaw bone and having a structural part (4) associated with said post part, to which structural part a denture piece can be attached, the structural part comprising an integrally molded contact pin (8) which can be placed in an associated shaped recess (10) in the post part (2) with a positive fit, it is to be possible on the one hand to suitably index the implant in a simple and reliable manner, on the other hand a particularly high level of mechanical stability against rotation being ensured, even with an overall height which is kept low.

13 Claims, 23 Drawing Sheets

(56) References Cited

U.S. PATENT DOCUMENTS

| | | |
|---|---|---|
| 8,226,410 B2 | 7/2012 | Kim |
| 2006/0240384 A1* | 10/2006 | Fraccon ................ 433/173 |
| 2006/0252009 A1 | 11/2006 | Gogarnoiu |
| 2007/0037123 A1* | 2/2007 | Mansueto et al. ........ 433/173 |
| 2007/0190491 A1 | 8/2007 | Blackbeard |
| 2008/0241789 A1 | 10/2008 | Mundorf |
| 2008/0261176 A1* | 10/2008 | Hurson ................ 433/174 |
| 2009/0305190 A1 | 12/2009 | Zipprich |
| 2010/0240009 A1 | 9/2010 | Gogarnoiu |
| 2011/0065064 A1* | 3/2011 | Kahdemann et al. ..... 433/174 |
| 2012/0237899 A1 | 9/2012 | Holmstrom et al. |
| 2012/0288826 A1 | 11/2012 | Fitton, III |

FOREIGN PATENT DOCUMENTS

| | | |
|---|---|---|
| EP | 1203567 A2 | 5/2002 |
| EP | 2106767 A1 | 10/2009 |
| JP | H10-57402 | 3/1998 |
| KR | 10-2004-0081320 | 9/2004 |
| KR | 10-2004-0081320 | 10/2004 |
| RU | 2202984 C1 | 4/2003 |
| RU | 34862 U1 | 7/2003 |
| WO | 93/02632 A1 | 2/1993 |
| WO | 01/28451 A1 | 4/2001 |
| WO | WO 2006/109176 * | 10/2006 |
| WO | WO2007121939 A1 * | 11/2007 |
| WO | 2008/128756 A2 | 10/2008 |
| WO | 2008155136 | 12/2008 |

OTHER PUBLICATIONS

International Search Report received in PCT/EP2009/007702, mailed Mar. 16, 2010.

International Preliminary Report on Patentability and Written Opinion received in PCT/EP2009/07702. Mailed Feb. 22, 2011.

* cited by examiner

Height of lift ΔH of the structural part comprising an elliptical integrally moulded contact pin in an elliptically adapted shaped recess in the post part with a rotatory offset contact angle ω about the axis of the integrally moulded contact pin

DENTAL IMPLANT

CROSS-REFERENCE TO RELATED APPLICATIONS

This application is a 371 National phase entry of PCT/EP09/07702, filed 28 Oct. 2009.

FIELD OF THE INVENTION

The invention relates to a dental implant comprising a post part which can be placed in a jaw bone and comprising a structural part associated with said post part, to which structural part a denture piece can be attached, the structural part comprising an integrally moulded contact pin which can be placed in an associated shaped recess in the post part with a positive fit.

BACKGROUND OF THE INVENTION

Dental implants of this type are known in a variety of forms. They are normally inserted into the jaw bone in place of a tooth which has been extracted or has fallen out in order to retain, after a healing phase of three to four months, either a prosthetic part acting as a denture or else a crown. For this purpose a dental implant of this type is normally formed as a suitably shaped metal member, the post part normally being inserted into the jaw bone by being screwed in at the point provided. The post part generally comprises, at the apical end, a mostly self-cutting thread with which the post part is inserted into the accordingly prepared implant bed.

A dental implant of this type is normally basically formed in two parts and comprises the post part provided for placement in the jaw bone and an associated structural part to which the denture piece provided as a prosthesis or the like can be attached. The post part and also the head part or structural part normally consist of metal or a ceramic material, more specifically in particular of titanium, zirconium, a titanium alloy, zirconium alloy, a titanium-containing alloy, a zirconium-containing alloy, a zirconium oxide-aluminium oxide ceramic material, or a ceramic material which contains either zirconium oxide or aluminium oxide or comprises at least one of the ceramic materials as a main constituent. Furthermore, ceramic materials can be used which are based on silicon or silicon oxide and contain, for example, nitrogen, hydrogen, carbon or tungsten. The post part is normally provided on its outer face with a thread which may be configured as a self-cutting thread or else as a non-self-cutting thread. The post part is normally anchored in an accordingly prepared implant bed of the jaw bone. The construction of the thread provided in the outer region of the post part is normally designed for high primary stability of the arrangement and uniform transfer into the jaw bone of the forces produced during chewing loading of the dental implant.

The structural part, the upper region of which is normally equipped, in a manner which is known per se, with a crown, another prosthetic provision or the like, is normally screwed to the post part via a suitably selected connecting screw. When fixing in place, the thread of the connecting screw is normally screwed into an associated inner thread in the post part. During the screwing-in process the screw head of the connecting screw presses the structural part onto the post part via an indentation in the end of said structural part. However, the structural part can also be pressed into the post part and be fixed merely via jamming, or can be fixed by cementing/bonding.

In order to stabilise this arrangement, a contact pin is normally integrally moulded on the structural part and can be introduced into an associated shaped recess in the post part with a positive fit. The structural part can thus be inserted via the contact pin into the shaped recess in the post part, mechanical fixing then normally being achieved by tightening the connecting screw. Of course, in the manner of a reverse arrangement, the contact pin may also instead be integrally moulded on the post part and the shaped recess may be formed in the structural part.

BRIEF SUMMARY OF THE INVENTION

The embodiments below are based on the more widespread variant in which the contact pin is formed on the structural part and the shaped recess is formed in the post part; however the subject-matter of the invention naturally also includes the corresponding further variant in reverse arrangement, in which the contact pin is arranged on the post part and the shaped recess is arranged in the structural part.

With regard to the forces produced during chewing loading and the longevity desired with use of a dental implant of this type, the mechanical stability of the arrangement under various loads is of considerable importance. In particular, a rotation or twisting between the structural part and the post part owing to external forces, usually caused by the chewing loading, is generally also to be counteracted. For this purpose a mechanical indexing in the form of a mechanical lock is normally used, or the surface pressure between the structural part and the post part is suitably selected. In particular, for indexing and in order to avoid rotation of the structural part on the post part, a suitable contouring both of the cross-section of the contact pin and of the shaped recess associated therewith may be provided in order to form the aforementioned mechanical lock. For this purpose the contact pin and accordingly also the shaped recess are normally hexagonal in cross-section. Alternatively, however, configurations as Torx or 'multitude systems' with varying numbers of elements and of varying geometry are known.

However, depending on the point of placement of the dental implant (anterior tooth region, posterior tooth region, lower jaw, upper jaw), the bone substance, the other remaining teeth, and the course and position of the vessels and nerves, it is not always possible for the practitioner to drill the hole for the post part or implant so as to match the shaft of the prosthetic provision provided, i.e. in particular of the crown or the like. It is thus possible that a straight or linear post part or implant and/or a straight or linear structural part do not satisfy the anatomical requirements of the patient and his treatment. In order to overcome this problem, angular or 'angled' structural parts are also used as necessary.

The angle of inclination normally provided in this regard generally lies in a range between 10° and 30°, but may also be up to 45° -60°. In systems of this type, once the implant has been placed in position, preferably once the post part has healed, the spatial and geometric information regarding the rest of the teeth (for example antagonists, teeth arranged mesially to and distally from the point of insertion), the mucous membrane, and the post part or implant or the assembled structural part must be ascertained in order to produce the crown, bridge or other prosthesis. This spatial and geometric information is necessary in order to produce the crown, bridge or the like in a manner which is optimised in terms of fit and anatomy. For this purpose an impression, preferably made of silicone or another dental impression material, of the oral situation is normally made. This impression is preferably filled with plaster or another dental modelling material. This plaster model is thus a duplicate of the patient's oral situation. It provides the dentist and/or the dental technician with information regarding the position of the remaining teeth, the mucous membrane and the inserted post part or implant.

In order to improve the transfer of position and geometry of the inserted post parts or implants, special impression posts made of metal and/or plastics material are preferably placed on and/or screwed onto the inserted post parts or implants. The impression is then made in the mouth, preferably with silicone. Once the impression material has set, the impression post either remains on the implant when the impression is removed or is removed with the impression. When the impression is filled, the impression post or structural post must be placed in the impression and connected to a laboratory implant. In terms of the connection and geometrically towards the impression post or structural post, this laboratory implant has a geometrical shape which is identical or similar to that of the inserted post part or implant. Once the impression with the integrated impression post or structural post and integrated laboratory implant has been filled, a plaster model with a laboratory implant cast therein is obtained.

If the implant system used has an indexing, this will have been transferred from the patient's mouth to the plaster model. Based on this plaster model, the prosthetic provision of the implant or implants is planned and produced. In this instance the rotatory position of the structural plant on the implant is key. If the implant system used has an indexing, the positioning options of the structural part on the laboratory implant are limited. In the case of a hexagonal connection, there are six positioning options. In the case of an implant system without indexing, all positions between 0° and 360° can be used. Once the denture has been produced, the fit in the patient's mouth is generally checked. During this check or else during the final fitting of the prosthetic denture, the practitioner must fit the structural part and all further prosthetic elements in the patient's mouth in the same position as on the plaster model.

In systems of this type the correct rotatory orientation of the denture in the patient's mouth following treatment is of particular importance. On the other hand, however, the actual treatment, i.e. the introduction of the structural part provided with the denture into the patient's mouth by connection to the ingrown post part, is to be kept as short as possible so as not to cause the patient too much stress during the treatment. In order to satisfy these two aims to the greatest extent possible, the structural part of such an implant system can be formed in a number of pieces, the pieces forming the structural part basically being formed so as to be freely rotatable relative to one another. In systems of this type the structural part and therefore the denture can be correctly orientated in the laboratory by suitable inspection of the oral situation and can also be suitably prepared. Once the structural part has been produced in the laboratory by assembly of the individual pieces with correct orientation, it can be introduced into the patient's mouth on the basis of prior indexing. For this purpose the contact pin with which the assembled structural part is placed in the post part is normally suitably indexed and multi-symmetrical, in such a way that only a relatively small number of possible orientations can be selected during insertion and therefore correct adjustment of the spatial orientation during insertion is possible in a particularly simple manner. Implant systems of this type with a multi-part structural part are known, for example, from DE 10 2006 018 726.

However, as has now been found, in such implant systems, in spite of the comparatively great advantages offered by pre-adjustment of the orientation in the laboratory, the structural part may be excessively tall or long as a result of the multi-part configuration of the structural part, so that such an implant system might not be adapted for use in all therapeutically necessary positions, possibly owing to reasons of space.

As a further design objective for such implant systems it should also generally be taken into consideration that a comparatively high level of tightness during mechanical contact between the structural part and the post part should be ensured in order to avoid infiltration of bacteria or the like into the inner implant region. In particular, the risk of inflammation of the tissue surrounding the dental implant, particularly in the tissue regions which are no longer readily accessible, is thus also to be kept to a minimum.

The object of the invention is therefore to provide a dental implant of the above-mentioned type with which it is possible on the one hand to suitably index the implant in a particularly simple and reliable manner, on the other hand it being possible to achieve a particularly high level of tightness between the structural part and the post part, even with an overall height which is kept low.

This object is achieved in accordance with the invention in that the cross-section of the contact pin integrally moulded on the structural part and the cross-section of the shaped recess associated with said contact pin each have a number of primary directions in which the radius in each case adopts a relative maximum value, and the outer contour of the cross-section is selected in such a way that it has precisely one tangent at each point. The outer contour is also preferably selected in such a way that it is intersected at at most two points by any straight lines.

The invention is based on the consideration that, particularly in view of the comprehensive covering of all possible insertion scenarios, the overall height of the structural part per se should be kept particularly low by basically forming the structural part in one piece. In order to still provide, in a simple manner, a suitable indexing which makes complex orientation and adjustment of the pre-prepared implant in the patient's mouth unnecessary, a corresponding orientation of the structural part should be ensured via the provision of a suitable cross-section of the contact pin and of the shaped recess, associated therewith, in the post part. For this purpose the radius of the cross-section of the contact pin and, accordingly, of the shaped recess, adapted thereto, in the post part, i.e. the radius or distance from the outer contour of the cross-sectional face to the central or middle point thereof, in particular the centre of gravity, based on rotation or pivoting thereabout, should not be constant, but instead should have maximum values in a number of primary directions, i.e. in particular in at least one primary direction. When the contact pin is inserted into the shaped recess these primary directions of both the contact pin and the shaped recess are overlapped, in such a way that the structural part attached to the contact pin is orientated as desired relative to the post part.

The respective maximum value of the radius as a function of the angle of rotation about the centre point or point of gravity of the cross-sectional face may be the absolute maximum or highest value of the radius or else a local or relative maximum value of the radius, at which the radius adopts a greater value in the respective primary direction than in the directly adjacent orientations.

In order to particularly reliably ensure the desired high level of tightness in the region of mechanical contact between the structural part and the post part, i.e. in particular between the contact pin and the inner face of the shaped recess, in such a system in which the structural part is orientated or indexed relative to the post part as a result of the contour, the outer contour of the cross-sectional face of the contact pin and, accordingly, of the shaped recess is suitably selected between the aforementioned primary directions. For this purpose the outer contour is substantially free from corners so that, in cross-section, each point of the outer contour has precisely one tangent.

In addition, a particularly high level of tightness can be achieved in that the outer contour is bulged or outwardly curved or rounded in the segments between the primary directions. As a result of this configuration, when the contact pin is inserted into the shaped recess any defects of form, i.e. for example local deviations in contour or the like between the cross-sections as a result of warping caused by production and any resultant local deformations, can be compensated for and the cross-sections can be adapted to one another. The outwardly curved or bulged configuration of the contour segments is similar to a criterion of an oval face, namely that any straight line intersects the respective cross-sectional face at two points at most.

In an advantageous configuration the outer contour of the cross-section is also selected in such a way that it corresponds to a segment of an oval in the regions between each two primary directions. In other words: the outer contour in the segments between each two primary directions additionally also advantageously satisfies the second criterion of an oval face, namely that precisely one tangent exists for each point of the contour segment. The outer contour in the respective segment thus extends in a relatively smooth manner without the formation of corners.

In a particularly advantageous development the dental implant is also formed in such a way that the contact pin integrally moulded on the structural part and the shaped recess in the post part associated with said contact pin are each formed completely with the avoidance of corners in the cross-sectional contour. The respective cross-section, even at the points of the outer contour in the respective primary directions, thus advantageously satisfies the second criterion of an oval face, namely that precisely one tangent also exists for these points, and thus as a whole forms an oval. The outer contour thus also extends in a rounded manner in the respective primary directions. It is ensured, particularly as a result of this relatively rounded course provided also in the primary directions, that any slight errors in orientation when the contact pin is inserted into the shaped recess are automatically corrected in the manner of guided self-centring without locks, clamps or catches.

In order to additionally ensure, in a particularly simple manner, the basically particularly desired high level of mechanical stability of the assembled system against rotation, the cross-section of the contact pin and, accordingly, also of the associated shaped recess should be selected, in a particularly advantageous development, so as to be bi-symmetrical or multi-symmetrical. Bi-symmetry can be achieved if the cross-section is advantageously elliptical, whereas tri-symmetry can be achieved if the cross-section is tri-oval in an alternative advantageous configuration.

In particular, owing to the aforementioned selection of the cross-section, said cross-section is basically bi-symmetrical or tri-symmetrical, in such a way that errors in the adjustment of the implants during insertion in the patient's mouth are virtually eliminated. If the elliptical or oval cross-section is bi-symmetrical, it can basically be described by two principal axes, as is conventional in particular for an ellipse, the first principal axis of the ellipse or of the oval describing the primary direction with a maximum diameter, and the second principal axis, which is generally perpendicular to the first principal axis, describing the secondary direction with minimal diameter of the ellipse or oval.

As has surprisingly been found, a particularly favourable insertion behaviour of the system, in which the structural part is orientated correctly in a self-centring manner when the contact pin is inserted into the associated shaped recess, can be achieved by suitably selecting the geometrical parameters in such a system, in particular by suitably selecting the ratio of the maximum diameter to the minimum diameter. For this purpose the contours of the cross-sections are advantageously each selected in such a way that the ratio of the minimum diameter to the maximum diameter of the ellipse or oval is at least 0.7 and at most 0.94, preferably at least 0.8 and at most 0.87.

With an elliptical configuration of the respective cross-sections, these parameters can also be specified equivalently by the 'numerical eccentricity' of the ellipse. In this case the numerical eccentricity of the ellipse is preferably between 0.35 and 0.7, particularly advantageously between 0.4 and 0.5.

In a particularly advantageous development the connection between the post part and the structural part is conical. For this purpose both the longitudinal extent of the contact pin of the structural part and the duct for receiving the contact pin formed by the associated shaped recess in the post part are each advantageously conical. Particularly in combination with the elliptical or oval cross-section, this conical configuration of contact pin and shaped recess means that there is still a relatively large amount of rotatory play when the contact pin is inserted into the shaped recess, in such a way that precise orientation or adjustment of the structural part relative to the post part is not yet necessary at this moment. Rather, when inserting the structural part the dentist can position it in a relatively roughly orientated manner since, when the contact pin first enters the shaped recess, the difference in area and the rotatory play caused thereby is still comparatively large owing to the conical configuration of the two parts.

However, as the contact pin is inserted further into the shaped recess, the sizes of the cross-sections are increasingly matched, in such a way that the rotatory play is automatically reduced as a result of the insertion and the structural part is therefore orientated in the rotatory direction in an increasingly precise manner. Once the contact pin has been inserted fully, i.e. as soon as the contact pin mechanically contacts the shaped recess with a positive fit, a virtually play-free and completely correct orientation is ensured. The conical configuration of the aforementioned components also additionally results in locking or self-locking of the two parts which, in particular with a tightened connecting screw, produces a particularly reliable positive and non-positive fit between the components and thus provides a particularly high mechanical stability of the entire system, even against rotation.

A highly precise and reliable transfer of forces and torques, virtually free from rotatory play, is thus also made possible.

In order to promote yet further this desired effect of automatic self-orientation of the structural part upon insertion of the contact pin into the shaped recess, the conical angles for the contact pin and/or the shaped recess is advantageously selected between 1° and 15°, preferably between 4° and 10°, particularly preferably approximately 6°. Particularly simple and reliable handling of the system, in particular in terms of a simple and uninterrupted insertion of the structural part into the post part, is ensured specifically as a result of such a parameter selection and particularly in combination with the above-mentioned geometrical parameters for the cross-section, in particular by the rounding of the corners in cross-section.

In a further advantageous configuration the structural part is assembled on the post part via a connecting screw.

In particular, the advantages afforded by the invention are that, upon insertion into the post part, it is possible to achieve reliable orientation of the suitably pre-prepared structural part provided with a denture, in a simple and mechanically stable manner, as a result of the appropriate contouring and parameterisation of the cross-section for the contact pin of the structural part and the associated shaped recess in the post part (or vice versa accordingly). The treatment period for the patient during insertion of the structural part into the oral cavity can thus be kept particularly short, it still being possible to achieve a particularly high-quality orientation of the denture. A reliable and simple orientation of the structural part can also be ensured by inserting the contact pin in the receiving duct, specifically as a result of the combination of a conical configuration of the duct receiving the contact pin and of the contact pin itself with the elliptical or oval cross-section of contact pin and receiving duct. In particular, a particularly high level of positioning accuracy can be achieved which is promoted yet further by the rotatory self-centring, which is provided owing to the cooperation of the components, during insertion of the contact pin.

BREIF DESCRIPTION OF THE DRAWINGS

An embodiment of the invention will be described in greater detail with reference to drawings, in which.

In all figures like parts are denoted by like reference numerals.

DETAILED DESCRIPTION OF THE INVENTION

Figure 1:
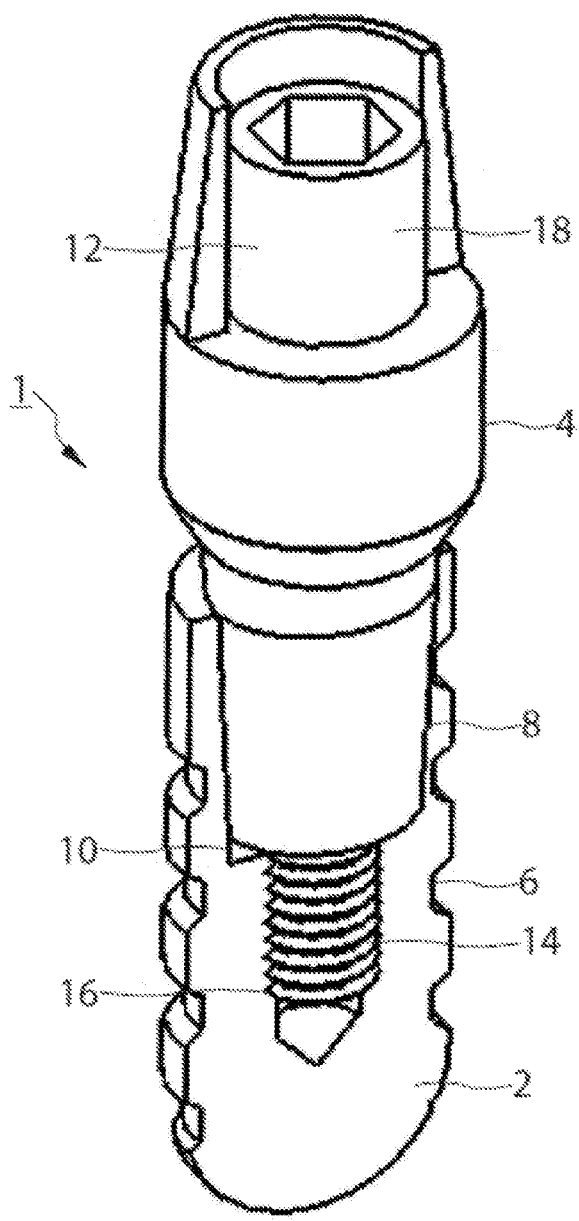
FIGS. 1, 2 are schematic views of a dental implant.
Figure 2:
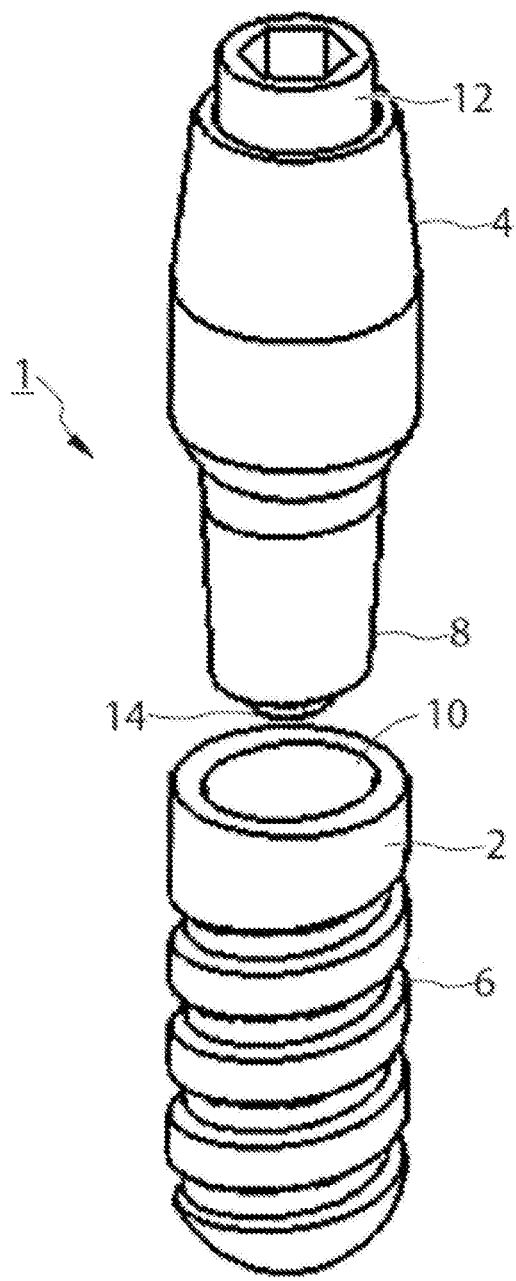

The dental implant 1 shown in FIG. 1 comprises a post part 2 provided for placement in a jaw bone and a structural part 4 associated with said post part. The one-piece structural part 4 in the embodiment is provided to be equipped with a denture piece, a crown or a prosthesis. In order to place the dental implant 1 in the patient's mouth the post part 2 is first inserted into the jaw bone in a first treatment step. For this purpose the post part 2 comprises an external thread 6 so that it can be inserted into the jaw bone by being screwed in. For this purpose, in the embodiment the thread 6 is formed as a self-cutting thread. The pitch of the thread 6 can be uniform or else can vary, it also being possible to take into consideration any different biological conditions or the like as well as different growing-in behaviour by suitable parameter selection. The construction and design of the thread 6 are configured in particular in view of a desired high primary stability and a uniform transfer of the forces produced in the jaw bone during chewing loading of the dental implant 1.

Once the post part 2 has been placed in the jaw bone a healing phase of four weeks to six months is provided, during which the post part should grow into the tissue and the jaw bone. In a second treatment step the structural part 4 comprising the attached denture piece can then be inserted. If the bone conditions are particularly favourable and a correspondingly high level of primary stability is provided, the structural part 4 and the further prosthetic components may also be supplied directly after insertion of the post part or implant.

In order to produce a relatively stable mechanical connection between the post part 2 and the structural part 4 in a simple manner, a contact pin 8 is integrally moulded on the structural part 4 and, when the post part 2 and structural part 4 are connected, can be inserted into a shaped recess 10 in the post part 2, which recess forms a duct for receiving the contact pin 8. The mechanical connection between the post part 2 and structural part 4 is produced via an associated connecting screw 12, of which the outer thread 14 is screwed into an inner thread 16 provided in the post part 2. The screw head 18 of the connecting screw 12 presses the structural part 4 onto the post part 2.

With suitable preparation of the structural part 4, the dental implant 1 is purposefully designed to ensure a reliable and mechanically stable rotatory orientation of the structural part 4, even when relatively high forces are produced, in particular by the chewing loading. In particular, it should also be possible to insert and incorporate the structural part 4 provided with the denture piece into the post part 2, which has grown into the jaw bone, over a relatively short treatment time.

For this purpose, in the embodiment the contact pin 8, which can be inserted into the associated shaped recess 10 in the post part 2 with a positive fit, and also the shaped recess 10 in the post part 2 each have an elliptical or oval cross-section. In addition, both the contact pin 8 of the structural part 4 and the shaped recess 10 in the post part 2, as well as the duct formed thereby for receiving the contact pin 8, are all conical. The free cross-section both of the contact pin 8 and of the shaped recess 10 tapers towards the end of the post part 2 in such a way that the receiving duct, formed by the shaped recess 10, in the post part 2 basically forms a type of funnel-shaped duct with an elliptical or oval cross-section. It is thus ensured that the cross-section of the contact pin 8 has, at the end thereof, an area which is relatively small compared to the inlet opening, formed by the shaped recess 10, in the post part 2, in such a way that when the contact pin 8 enters the shaped recess 10 there is a relatively large difference in area and therefore a relatively large amount of rotatory play between the aforementioned components.

It is thus sufficient when inserting the contact pin 8 into the shaped recess 10 for the structural part 4 to be orientated merely relatively roughly in the rotatory direction. As a result of the conical receiving duct, which constricts in a funnel-shaped manner and has an elliptical or oval cross-section, the respective cross-sectional areas are increasingly matched as the contact pin 8 is inserted further into the shaped recess 10, i.e. during insertion of the structural part 4 into the post part 2, in such a way that the contact pin 8 and therefore the structural part 4 is increasingly guided mechanically by the resulting positive fit. Once the contact pin 8 has ultimately been fully inserted into the shaped recess 10 and fits positively therein, the surfaces form a continuous positive connection in such a way that even the rotatory orientation of the structural part 4 is thus clearly determined. As a result of the insertion the structural part 4 can thus be automatically orientated, merely owing to the shape and contouring of the contact pin 8 and shaped recess 10, in such a way that no further adjustment by the dentist is necessary upon insertion of the denture.

Figure 3:
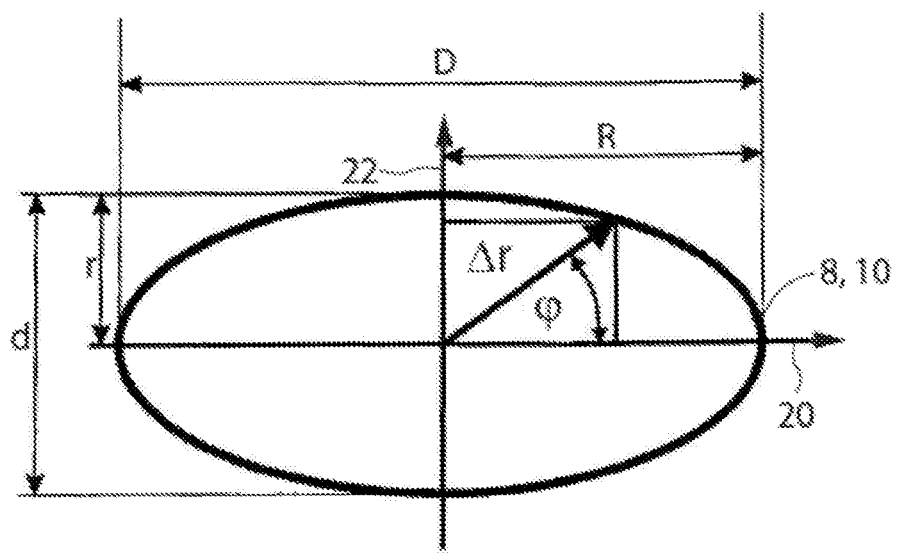
FIG. 3 is a cross-sectional view of a contact pin integrally moulded on a structural part of the dental implant according to FIG. 1.

As can be seen in the cross-sectional view in FIG. 3, in this embodiment the contact pin 8 (and with this accordingly also the associated shaped recess 10 in the post part 2) integrally moulded on the structural part 4 has a substantially elliptical cross-section which is quantitatively characterised (as is normal for an ellipse) by a first principal axis (indicated in FIG. 3 by the arrow 20) having a maximum diameter D and a second principal axis (indicated in FIG. 3 by the arrow 22) having a minimum diameter d.

The linear eccentricity e of this ellipse is described, in accordance with the conventional definition, by the formula $e=\sqrt{D^2/4-d^2/4}$, whereas the 'numerical eccentricity' $\epsilon$ of the ellipse is given by the equation $\epsilon=2e/D$. The numerical eccentricity of an ellipse may have a value between 0 and 1. A circle has an eccentricity of 0.

In order to particularly facilitate the incorporation of the denture when connecting the structural part 4 to the post part 2 and to particularly promote the desired contour-related self-centring upon insertion, the geometrical parameters of the contact pin 8 and shaped recess 10 are selected in accordance with the following criteria:

The greater the eccentricity of a conical-elliptical connection, the better the mutual positioning of the components. However, based on the mechanical properties and mechanical strength, a high eccentricity is rather unfavourable, in particular since the maximum implant diameter of the post part 2 is limited. The diameter of a post part 2 is normally between 2.5 mm and 6 mm. The greater the eccentricity, the more irregular the wall thickness of the post part 2 and of the structural part 4. Extensive studies of prototypes have revealed that the numerical eccentricity $\epsilon$ should not be less than 0.3 and, for particularly favourable positioning, is preferably not less than 0.35. Conversely, so as not to excessively reduce the strength of the post part 2, structural part 4 and, where necessary, the connecting screw, strength studies with prototypes have revealed that the numerical eccentricity $\epsilon$ should not be greater than 0.7 and preferably is not greater than 0.8. A most preferred combination of good positioning and high strength was achieved with numerical eccentricity values c between 0.4 and 0.5.

Figure 4:
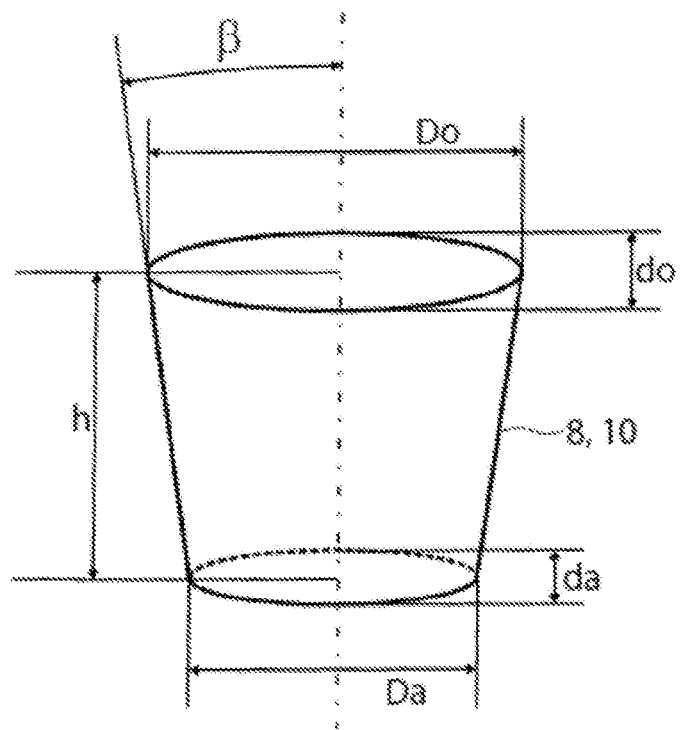
FIG. 4 shows the shaped recess provided in the post part to receive the contact pin of elliptical cross-section according to FIG. 3.
Figure 5:
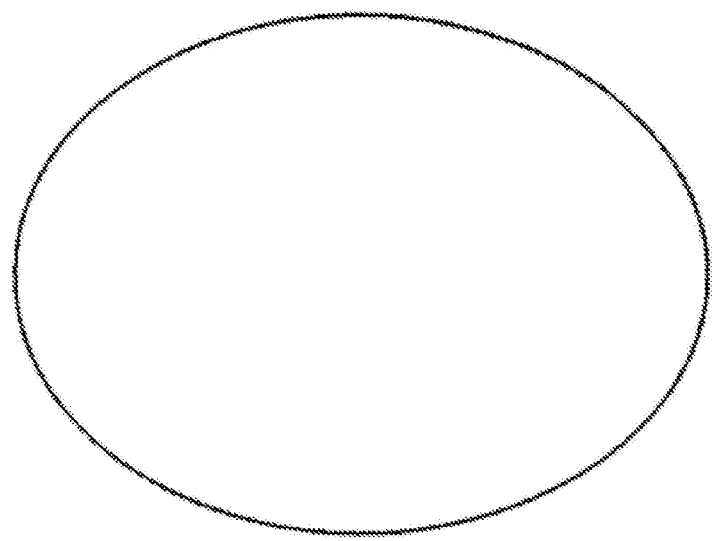
FIGS. 5-40 show, in pairs, an alternative cross-sectional shape for the contact pin of the dental implant and the associated shaped recess.
Figure 6:
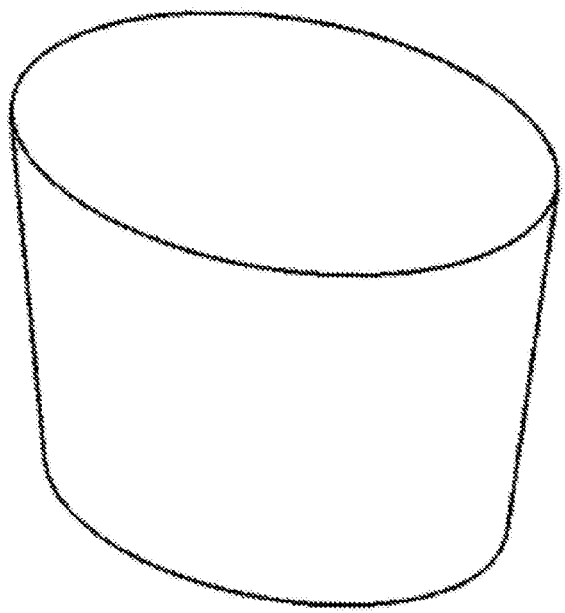
Figure 7:
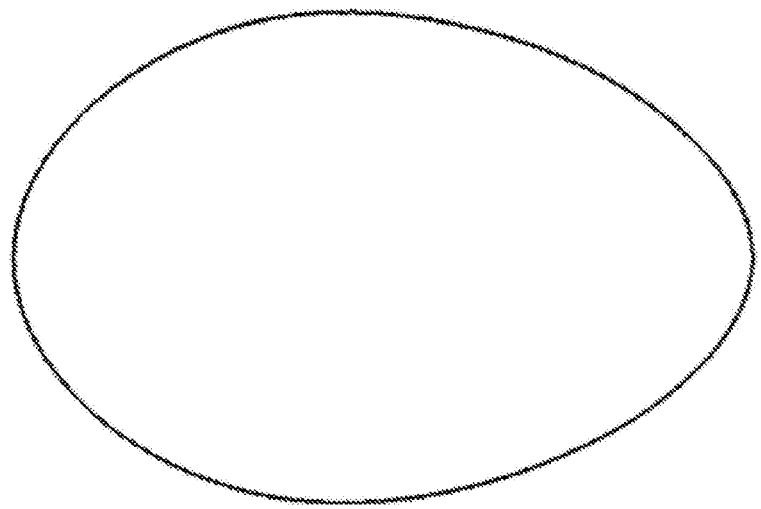
Figure 8:
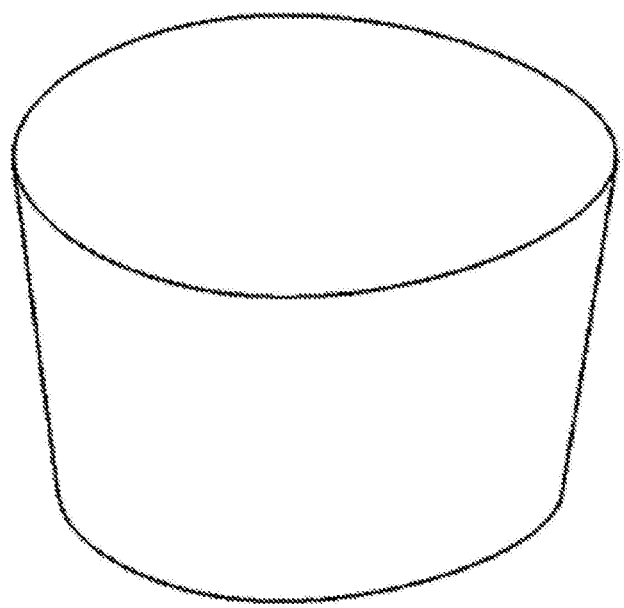
Figure 9:
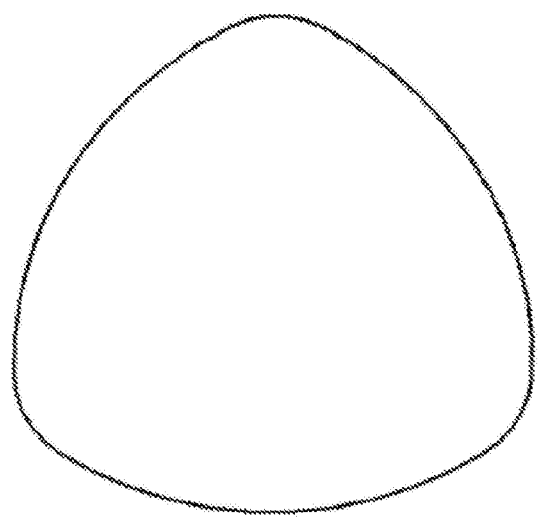
Figure 10:
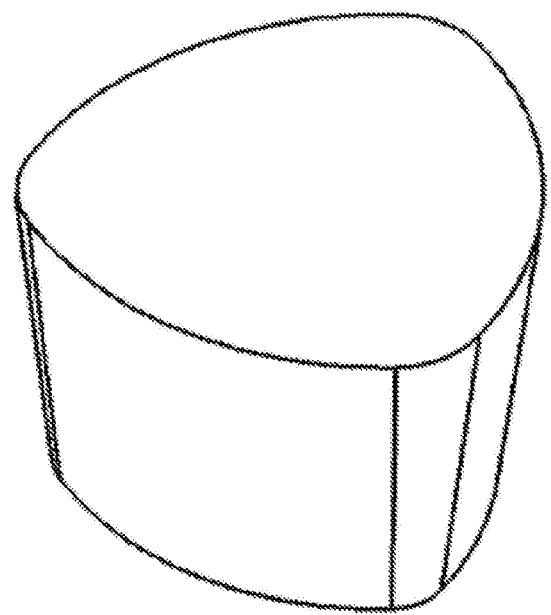
Figure 11:
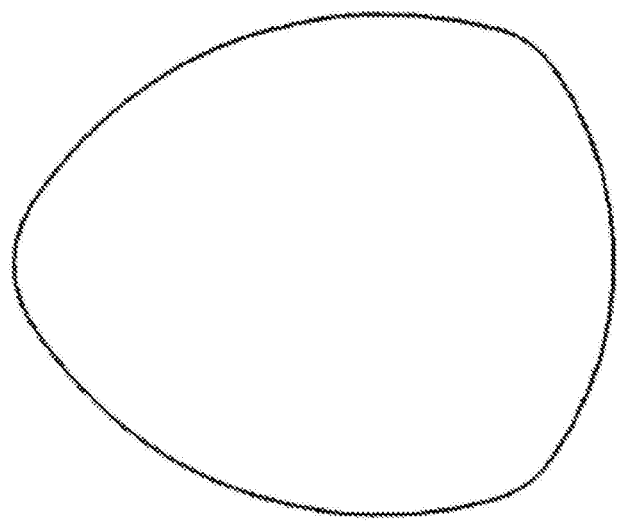
Figure 12:
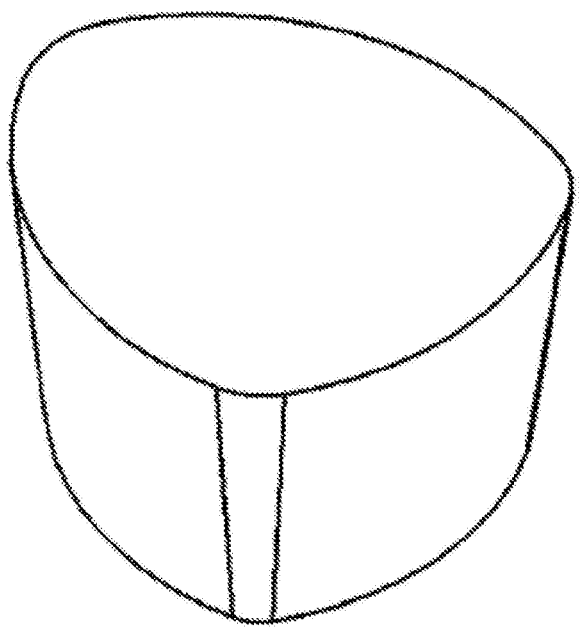
Figure 13:
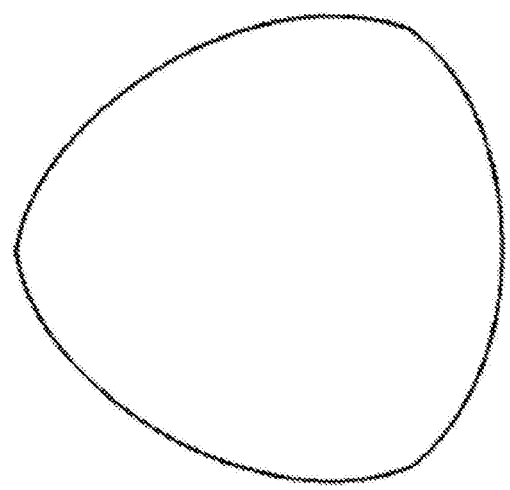
Figure 14:
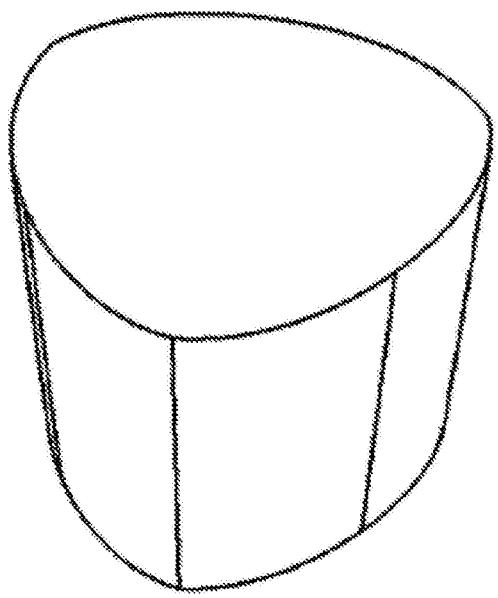
Figure 15:
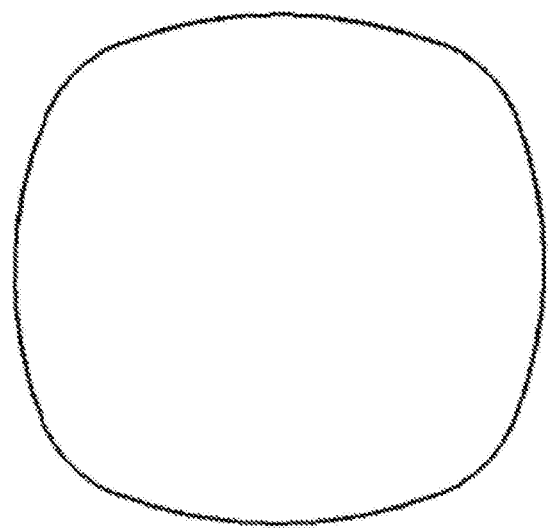
Figure 16:
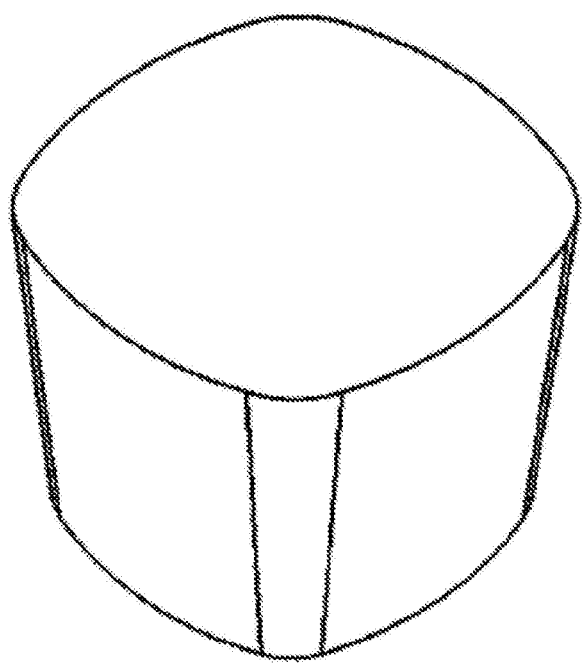
Figure 17:
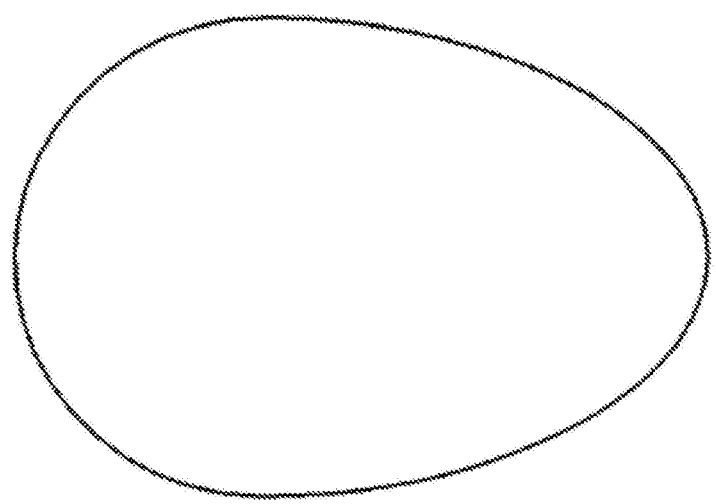
Figure 18:
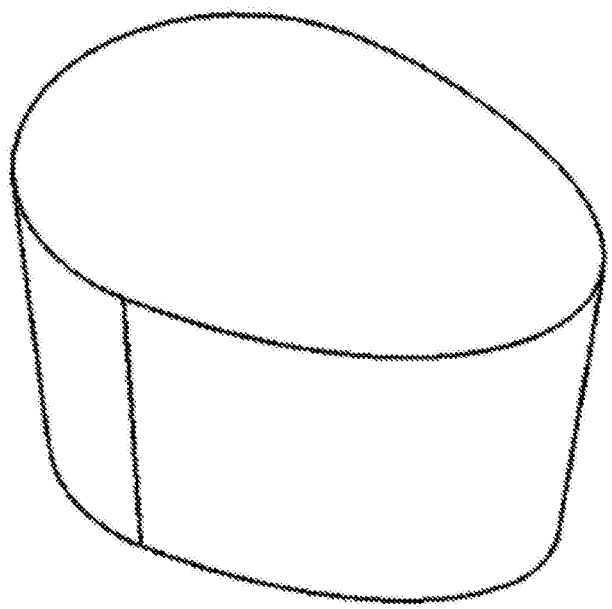
Figure 19:
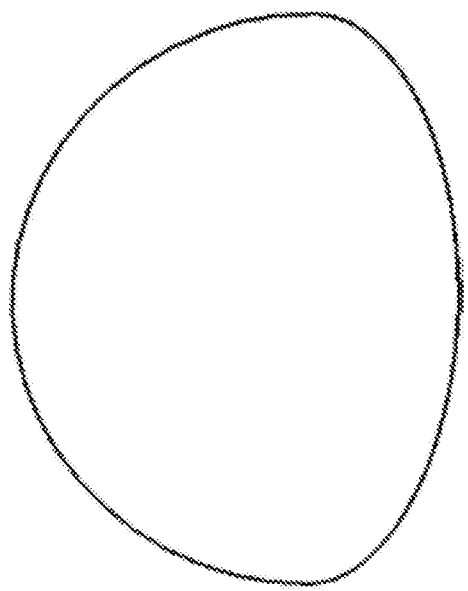
Figure 20:
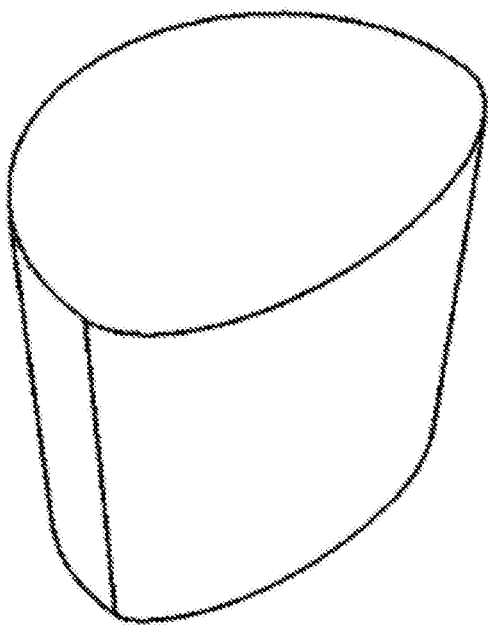
Figure 21:
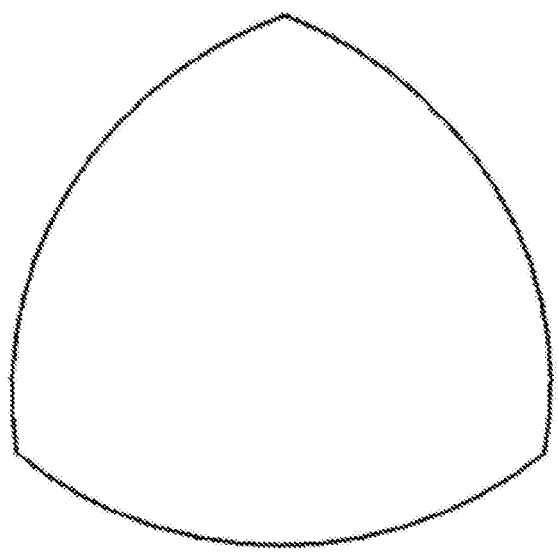
Figure 22:
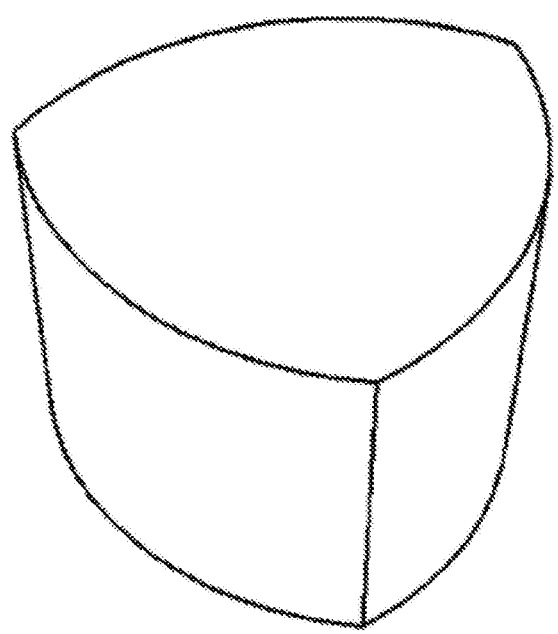
Figure 23:
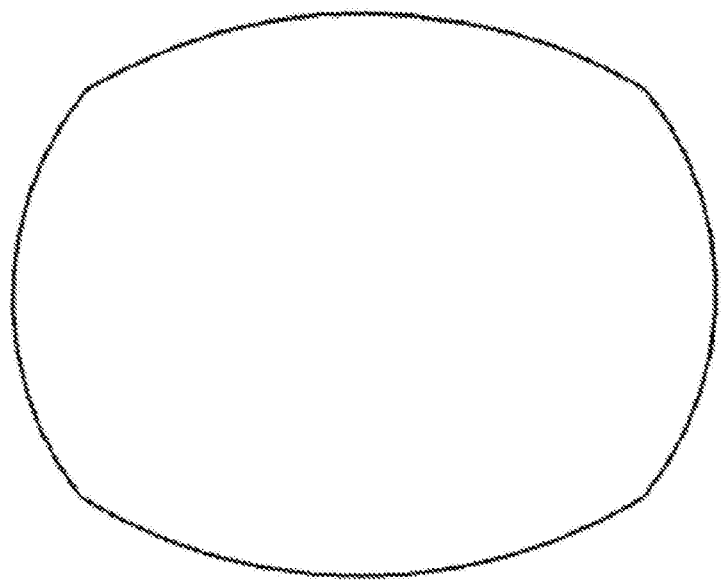
Figure 24:
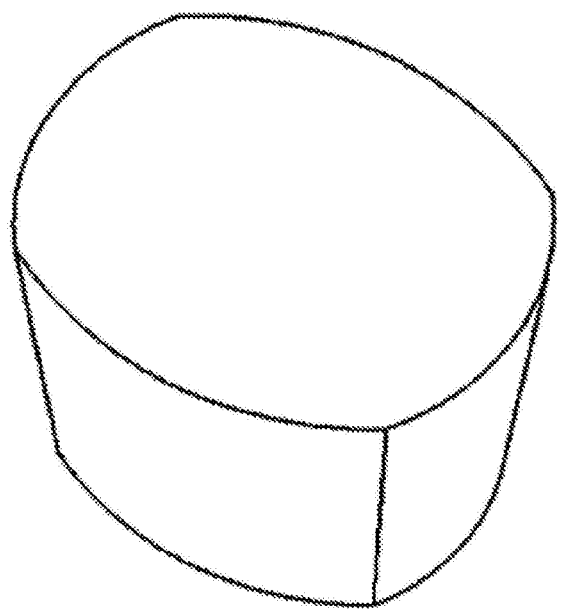
Figure 25:
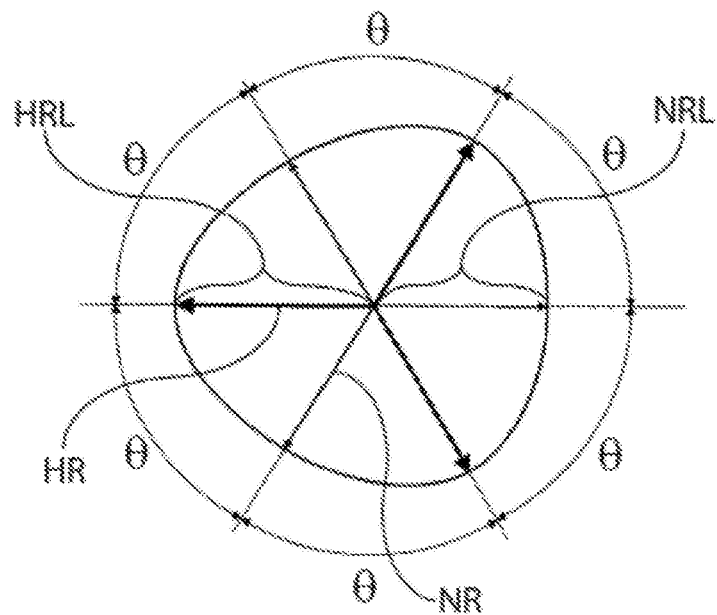
Figure 26:
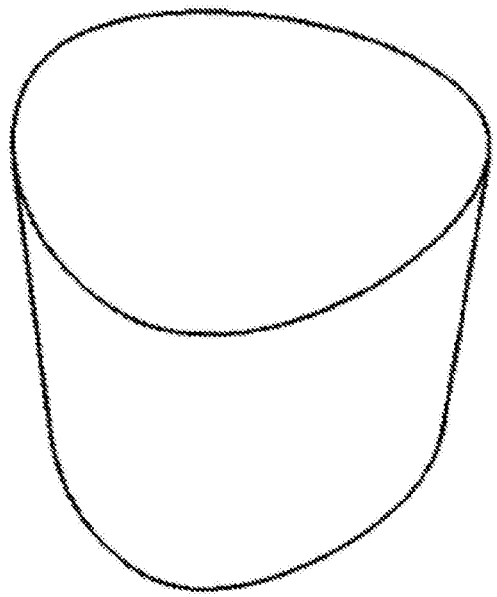
Figure 27:
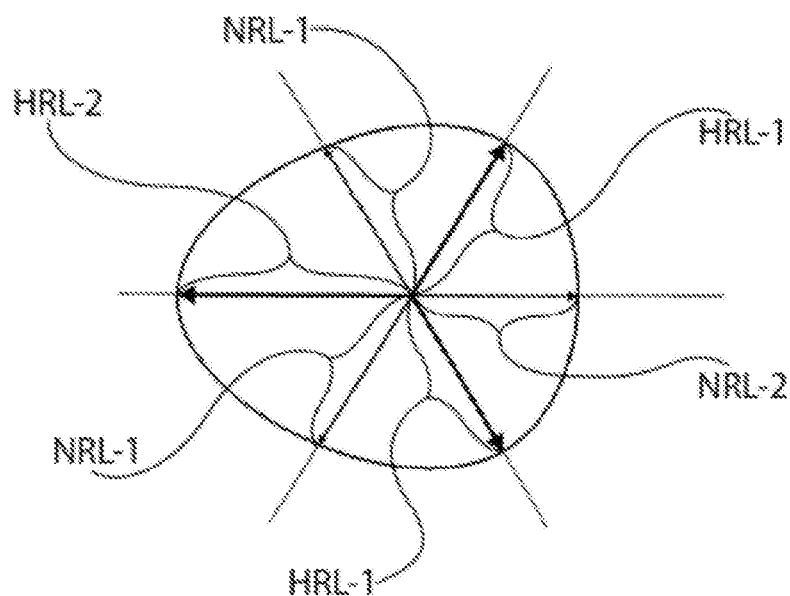
Figure 28:
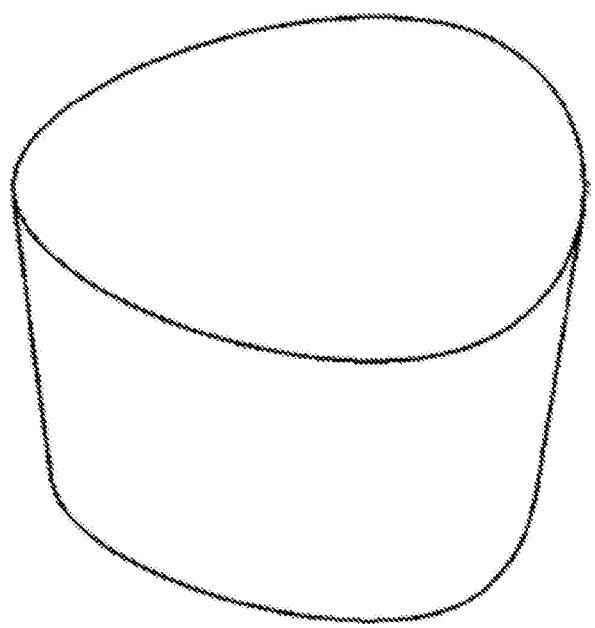

The conical form of both the shaped recess 10 and of the contact pin 8 adapted thereto in the contact region can be seen in FIG. 4. This conical region is characterised by the geometrical parameters of cone angle $\beta$, effective cone length h, maximum and minimum ellipse diameter at the occlusal end of the contact pin 8 $D_o$ and $d_o$, and maximum and minimum ellipse diameter at the apical end of the contact pin 8 $D_a$ and $d_a$. These geometrical parameters are preferably selected in accordance with the following criteria:

The more positioning options provided to the practitioner for a structural part 4 in the post part 2, the more difficult the positioning. A preferred optimum in terms of positioning is with merely 1 positioning option. However, if there is a conical indexing (for example one elliptical semicircle, one round semicircle), there is an unavoidable risk that the structural part 4 may be inserted incorrectly. If the connecting screw 12 is then tightened for fixing, either the post part 2 or the structural part 4 could be damaged. In order to avoid the risk of such damage, at least two positioning options are preferably provided. If there are at least two positioning options, although there is still a risk of damaging the components this can be avoided by targeted sizing. The risk is always present if the component is inserted so as to be rotatably offset by approximately 360°/(2*positioning options) and the connecting screw 12 is then tightened. With an elliptical or oval geometry, the indexing would be 360°/(2*2)=90°.

This risk is avoided with a particularly preferred selection of the geometrical parameters, in which either
1. the cone angle $\beta$ is selected as a function of the change in radius within the indexing geometry and the cone length h of the structural part 4, or another sequence of dependencies, in such a way that, with an offset by approximately 360°/2*positioning options, the structural part 4 cannot be inserted into the post part 2 and the thread 14 of the connecting screw 12 does not engage in the thread 16 of the post part 2. The thread 14 of the connecting screw 12 should only engage in the thread 16 of the post part 2 if the structural part 4 can be inserted into the post part 2 and if the rotatory offset from the end position is so slight that the structural part 4 will begin to self-centre in the post part 2 merely through the force applied by the connecting screw 12, without the static friction between the contact surfaces of the structural part 4 and the post part 2 hindering the self-centring process,
2. the cone angle $\beta$ is selected as a function of the change in radius within the indexing geometry, the cone length h of the structural part 4, or another sequence of dependencies, in such a way that, with an offset by approximately 360°/(2*positioning options), the thread 14 of the connecting screw 12 does not engage in the thread 16 of the post part 2. The thread 14 of the connecting screw 12 should only engage in the thread 16 of the post part 2 if the rotatory offset from the end position is so slight that the structural part 4 will begin to self-centre in the post part 2 merely through the force applied by the connecting screw 12, without the static friction between the contact surfaces of the structural part 4 and the post part 2 hindering the self-centring process.

The variant 1 is relatively unfavourable in terms of ease of assembly. The greater the eccentricity of the ellipse, the smaller the cone angle $\beta$, and the shorter the common conical contact surface between the structural part 4 and the post part 2, the greater the risk that the structural part 4 cannot be inserted into the post part 2 in any rotatory position. This means that the broader, apical elliptical region of the structural part 4 is larger than the narrow elliptical entry region of the post part 2.

The following formula describes $D_a$ as a function of the cone angle $\beta$, $D_o$ and the effective cone length h between the structural part 4 and the post part 2:

$$D_a = D_o 2h*tan(\beta)$$

$D_a < d_o$ is preferably selected for excellent ease of assembly. If $D_a \geq d_o$, then good ease of assembly is not provided since the structural part 4 cannot be inserted into the post part 2 in any rotatory position about the axis of its inherent contact pin.

With the variant 2 the ease of assembly is particularly favourable. The magnitude of the numerical eccentricity $\epsilon$, the size of the cone angle $\beta$ and the effective cone length h should be selected in such a way that the self-centring effect of the conical-elliptical connection is fully ensured once the connecting screw 12 engages in the thread 16 of the post part 2. This means that the height of lift of the structural part 4 comprising the elliptical moulded contact pin should be greater than the effective common thread length of the connecting screw 12 and post part 2 with rotation through approximately 90° about the axis of the inherent contact pin, and by approximately 360°/(2*positioning options) with tri-oval connections or similar configurations.

The height of lift $\Delta H$ is to be understood to mean the offset or displacement of the structural part 4 in its longitudinal direction which occurs when the structural part 4 is rotated relative to the post part out of a position of correct orientation, in which the cross-sections of the contact pin 8 and the shaped recess 10 overlap, into a position of "maximum rotation", in which the primary directions of the contact pin 8 point towards the intermediate positions of the shaped recess 10 between the primary directions thereof. The resultant mutual offset of the cross-sectional surfaces causes the structural part 4 to lift in its longitudinal direction, i.e. the 'lift', owing to the conical configuration of the receiving duct.

With particularly favourable sizing, the connecting screw 12 only engages if the pitch of the height of lift $\Delta H$ as a function of the contact angle $\omega$ is at least 5 µm/°. A pitch greater than 10 µm/° and in particular greater than 15 µm/° has proven to be particularly favourable.

The height of lift of the structural part in the post part as a function of the numerical eccentricity $\epsilon$, the cone angle $\beta$, the minimum diameter d of the second principal axis and the contact angle $\omega$ is described by the following formula:

$$\Delta H = \frac{Do - \dfrac{d}{\sqrt{1 - \varepsilon^2 \cdot \cos^2(\omega)}}}{\tan(\beta)}$$

Connecting screws 12 which are normally used in the connections between the structural part 4 and the post part normally have a thread pitch between 0.2 mm and 0.5 mm per revolution. Working on the assumption that at least two thread turns, preferably at least three thread turns and preferably at least four thread turns are to be provided between the connecting screw 12 and the post part 6, the height of lift of the structural part 4 in the post part 2 should be at least 0.4 mm at 90°. However, it is more favourable if the height of lift is greater than 0.6 mm and, in particular, is at least 1 mm. This means that it is possible to ensure sufficiently bearing thread turns, the thread only engaging with favourable rotation (<90°, namely with a rotation in which the self-centring functions by means of the tension force which is applied by the connecting screw 12 when this is tightened between the structural part 4 and the post part 2.

Alternative cross-sections of the contact pin and the associated shaped recess are illustrated in the further FIGS. 5 to 40.

The advantages of conical connections between the structural part and the post part are already known in principle. In the case of conical connections, in particular with loads eccentric to the axis of the post part, force is transferred in a planar manner from the structural part to the post part. Furthermore, a large amount of the force to be transferred to the post part can be transferred directly thereto since the structural part is supported directly in the post part. This relieves the connecting screw, which is to fix the structural part and the post part. This effect can be observed with cone angles $\beta$ which are less than 45°. The cone angle is preferably less than 15°. In this way a premature loosening of the connection is prevented. This mechanical stabilisation acts as a virtually play-free locking mechanism against forces and/or bending moments acting extra-axially to the post part.

A further advantage of conical connections is the tightness between the structural part and the post part. In this instance it is particularly important for the geometry of the contact pin integrally moulded on the post part and the shaped recess formed in the post part to be round and adapted to one another. The only drawback is that the protection against rotation between the structural part and the post part is only provided with static friction between the two parts and there is no indexing for positioning. This is normally achieved by additional contact pins integrally moulded on the structural part. Structural parts are also known which first have one conical contact pin from the occlusal end, on which contact pin a first contact pin provided with a locking mechanism is attached in the apical direction, and in only a few cases a third contact pin is attached apically from the second contact pin. These geometries are then incorporated in the corresponding post part as negatively formed shaped recesses, in such a way that a combination of extra-axial and rotatory locking mechanisms can be achieved which is also used as indexing.

The objective is to combine, in a single geometry, a contact pin which is integrally moulded on the structural part and has an extra-axial locking mechanism with a rotatory locking mechanism which can be used as very precise indexing. This would also reduce the overall height of the contact pin without impairing the mechanical properties. This is achieved in accordance with the invention in that the geometry of the contact pin integrally moulded on the structural part corresponds to an oval and satisfies the geometric laws thereof. The geometry of the shaped recess formed in the post part is naturally adapted to the geometry of the contact pin attached to the structural part and the two are matched to one another. This also retains the advantages of a round, conical connection in terms of tightness.

Tests have shown that liquids and bacteria may infiltrate if the connection between the structural part and the post part is not tight. This may in turn have an impact on bone degradation at the post part. Further consequences may include bad breath and receding of the soft tissue, which can be associated with poor appearance. This problem occurs, above all, if there is a relative movement between the structural part and the post part, since in this case the two act as a pump. The transfer of force with no relative movement and with a positive fit in combination with tightness between the structural part and the post part is consequently very important.

In the case of round conical connections, self-centring occurs in the mesio-distal and vestibular-oral direction. Furthermore, rotatory self-centring can also be achieved with suitable geometry by changing the round conical geometry into an oval geometry. The change from a round conical geometry to an oval geometry consequently merely results in advantages which perfect the connection between the structural part and the post part and therefore benefit the practitioner, the dentist and the patient.

Figure 39:
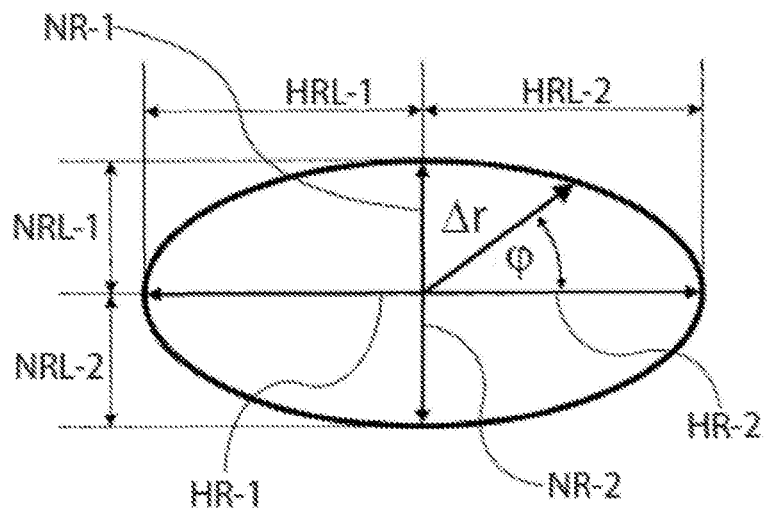

An ellipse can be described as a cyclic function $\Delta r_{(\phi)}$ about a centre which can be defined as follows:

An ellipse is shown in FIG. 39 for clarification.

Figure 43:
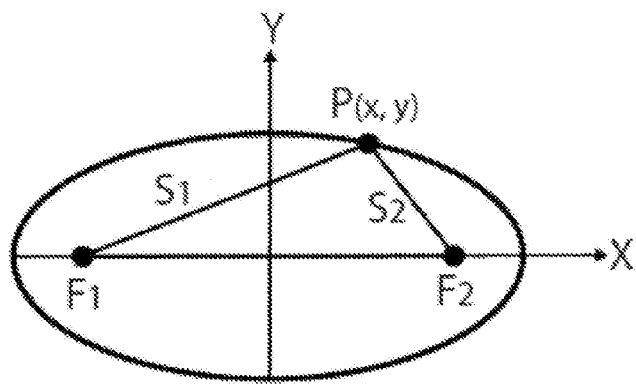
FIG. 43 is a schematic view of an ellipse.

There are two primary directions which are formed by two local maximums in $\Delta r_{(\phi)}$; both maximums have the same length and are parallel. Furthermore, there are two secondary directions which are formed by two local minimums in $\Delta r_{(\phi)}$; both minimums have the same value for $\Delta r_{(\phi)}$ and both minimums have the same length and are parallel. The angle between the primary directions and the secondary directions is 90°, whilst the angle between the primary directions is 180° and the angle between the secondary directions is 180°. All primary and secondary directions originate from the same point. The ellipse is characterised in that it corresponds to the laws of an oval (i.e. a straight line intersects the curve twice at most and each point on the curve has only one tangent) and, in addition, the curvature of the curve is different at each point between the primary and secondary directions. An ellipse consists of all points, of which the sum is equal to the distance between two fixed points $F_1$ and $F_2$ (FIG. 43). In FIG. 43 the sum is $S_1+S_2$. If such a geometry is used for the contact pin integrally moulded on the structural part and for the shaped recess in the post part, and if these are adapted to one another in size, then two positioning options will be given. In a particularly favourable embodiment the contact pin is formed conically on the structural part and the shaped recess is formed conically in the post part.

Figure 40:
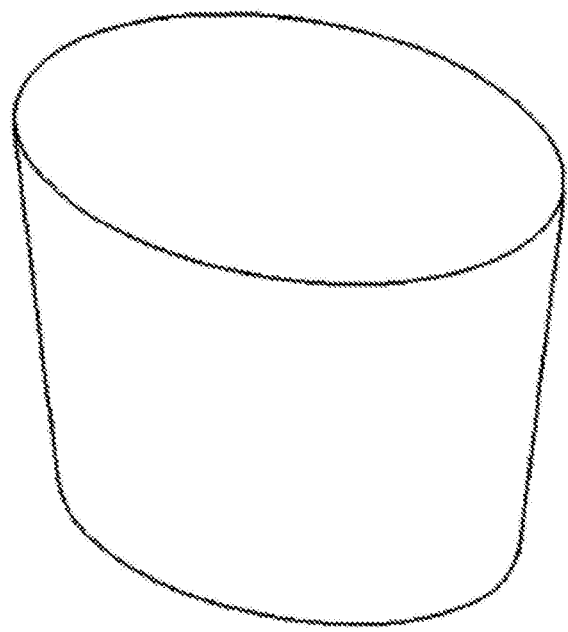

If it is now desired to increase the number of positioning options, but not to forego the extraordinarily good properties of the elliptical geometry, this can be achieved by increasing the number of primary and secondary directions, for example to 3 (FIG. 25), 4, 5, 6, 7, 8, 9 or more. In this case it is important that all primary and secondary directions originate from the same point, that the length of all primary directions is the same, that the length of all secondary directions is the same, that the angles between the adjacent primary directions are equal, that the angles between the adjacent secondary directions are equal, in a particularly favourable embodiment that the angles between the adjacent primary directions and the secondary directions are half the size of the angles between the adjacent primary directions and the angles between the adjacent secondary directions, that the number of primary and secondary directions is equal, that the curve between the primary directions and secondary directions satisfies the laws of an oval, and additionally that the curvature of the curve is different at each point between the primary and secondary directions. It is thus ensured that the number of primary directions and secondary directions gives the number of positioning options in which there is a positive and non-positive fit. A suitable geometry preferably has a maximum of four primary directions and four secondary directions (FIG. 31 and FIG. 32), in particular three primary directions and three secondary directions (FIG. 25 and FIG. 26), and in an optimum embodiment has two primary directions and two secondary directions and is thus an ellipse (FIG. 39 and FIG. 40). If four, five or six primary and secondary directions are used, geometries are produced such as those illustrated in FIG. 31 to FIG. 36, which are also favourable embodiments.

Eccentricity is caused by the difference in length between primary directions and secondary directions. If the secondary direction is too short in relation to the primary direction then the curvature changes from convex to concave and an oval is no longer provided (for example FIG. 37 and FIG. 38). The risk that the connection will not be tight is high as a result of manufacturing tolerances. The pressure between the structural part and the post part will also not be uniform, which encourages movement between the structural part and the post part. Furthermore, the difference between the length of the primary direction and the length of the secondary direction will be greater, which has a negative impact on the strength of the connection and the individual components. Extensive tests have shown that the secondary directions should preferably lie within the following ranges as a percentage of the primary directions.

| Number of primary and secondary directions | Minimum length of the secondary direction as a percentage of the length of the primary direction | Maximum length of the secondary direction as a percentage of the length of the primary direction |
|---|---|---|
| 3 | 70% | 95% |
| 4 | 80% | 97% |
| 5 | 90% | 98% |
| 6 | 95% | 99% |
| 7 | 96% | 99% |
| 8 | 97% | 99% |
| 9 | 98% | 99% |

When an oval and conical contact pin integrally moulded on a structural part is inserted into the corresponding shaped recess in a post part, there is contact between the two parts in the case of rotationally imprecisely orientated positioning of the structural part relative to the post part before the components are positioned relative to one another with a positive fit. This contact is not constant over the surface, but instead is linear or is provided at selected points. With rotatory positioning in degrees relative to one another in accordance with the formula 360°/(2×number of positioning options), the components can be fixed with a purely axial direction of insertion of the structural part into the post part. From a rotatory depositioning in degrees which is smaller or greater and unequal to a multiple according to the formula 360°/(2× number of positioning options) there is, with an axial direction of insertion and axial insertion force with virtually free rotatory movement of the structural part (i.e. rotatory influence on the position of the structural part almost exclusively by the post part), a rotatory self-orientation of the oval and conical contact pin integrally moulded on the structural part in the corresponding shaped recess in the post part. This rotatory self-orientation can also be described by the term rotatory self-centring.

With a particularly favourable configuration of an ellipse or of one of the other specific cases described of an oval with an equal or greater number of positioning options, secondary directions and primary directions, the connecting screw, which fixes the structural part to the post part, only engages when the rotatory self-centring can occur purely through the forces and/or torques generated by the connecting screw. This means that before the rotatory self-centring is possible purely as a result of the forces and/or torques generated by the connecting screw, the thread of the connecting screw has not yet reached the thread formed in the post part. Consequently, the height of lift of the structural part in the post part, with a rotational offset angle therebetween, is greater than the usable and common thread length between the connecting screw and the post part. If this were not configured in this manner, and instead the connecting screw were to engage in the post part before the rotatory self-centring caused by the forces and torques of the connecting screw can take place, this could lead to permanent damage of the post part which has healed in the patient's jaw bone. As a result the post part would be explanted from the patient's jaw. The risk is always present if the component is introduced rotationally offset by approximately 360°/(2×number of positioning options) and the connecting screw is then tightened. A geometry comprising three primary directions, three secondary directions and three positioning options would give 360°(2*3)=60°. With all described geometries as well as with the ellipse it is advantageous if the connecting screw does not engage in the thread of the post part before the forces and/or torques produced by the connecting screw are sufficient for the rotatory self-centring of the structural part in the post part. It is further advantageous if the geometries of the contact pin integrally moulded on the structural part and of the shaped recess provided for said contact pin in the post part therefor, the eccentricities, the length of the conical contact pin and the cone angle are dimensioned in such a way that the contact pin, with each revolution about its own axis, can penetrate the shaped recess formed therefor in the post part at least by a small extent, advantageously at least by 0.1 mm and in particular at least by 0.5 mm. This considerably facilitates the positioning of the structural part in the post part.

Figure 29:
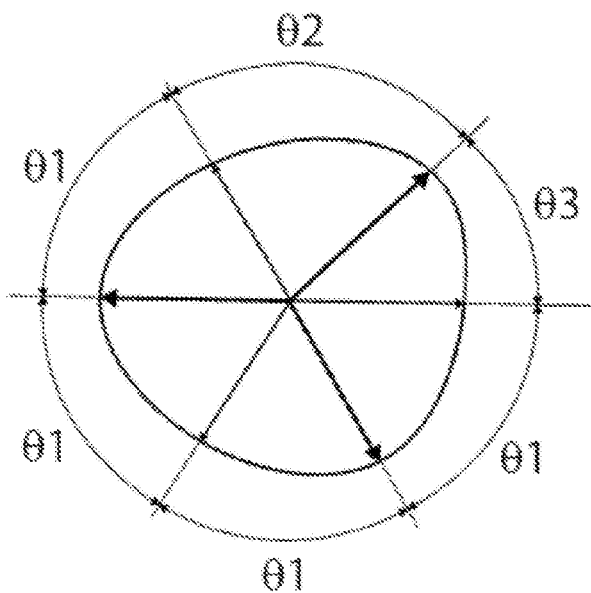
Figure 30:
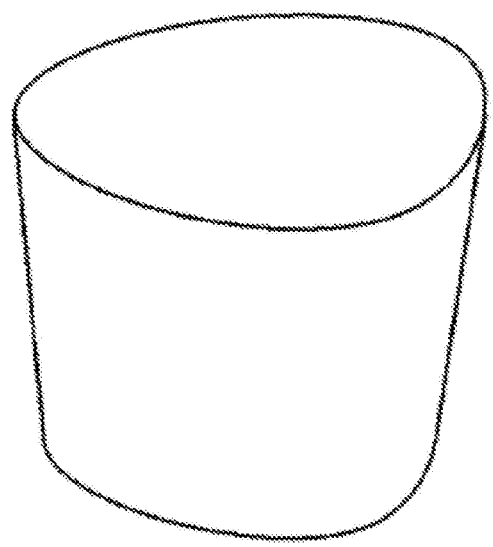
Figure 31:
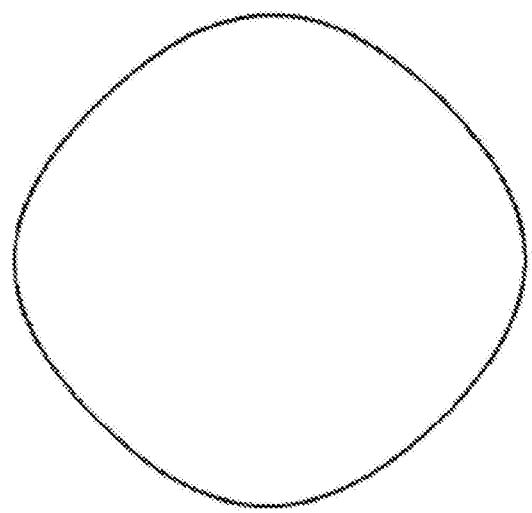
Figure 32:
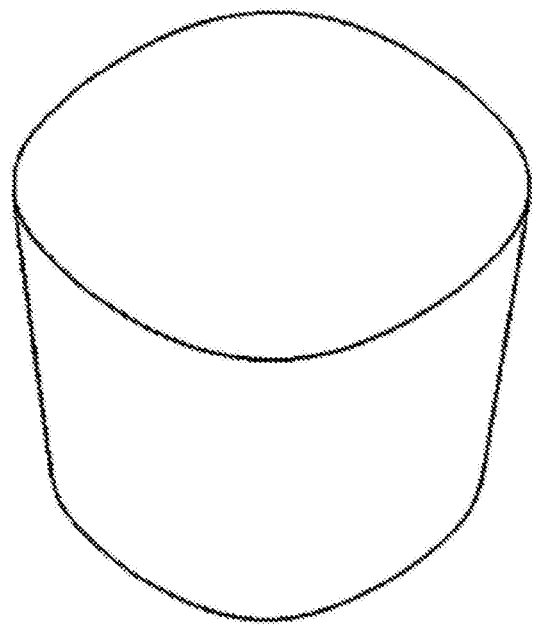
Figure 33:
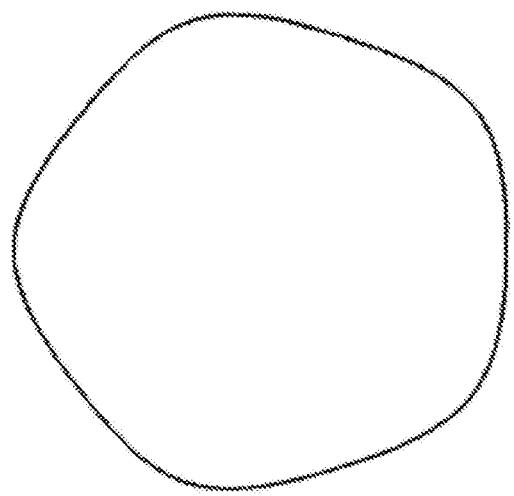
Figure 34:
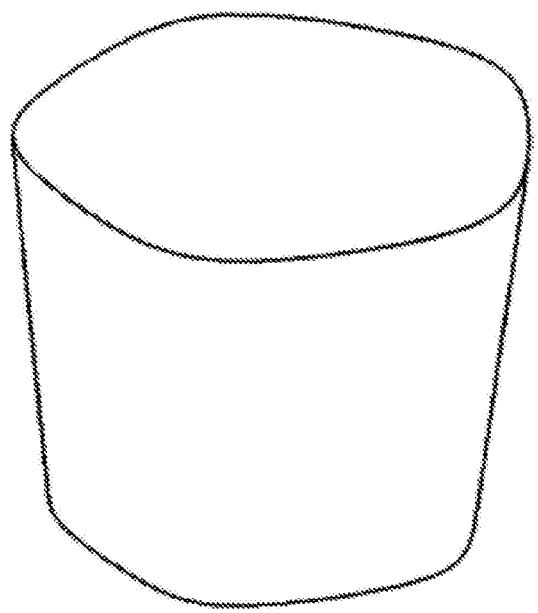
Figure 35:
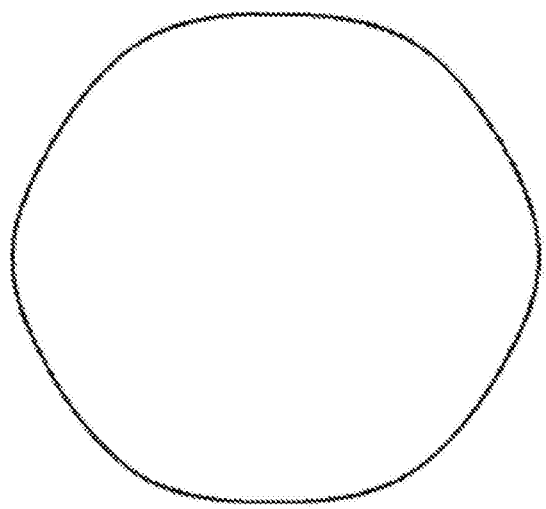
Figure 36:
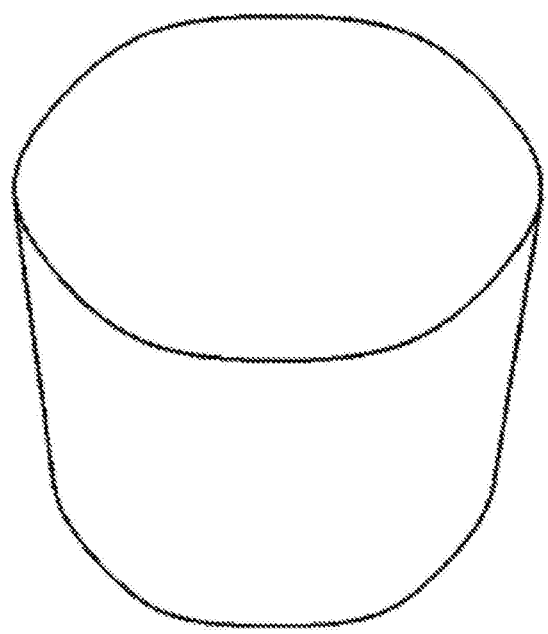
Figure 37:
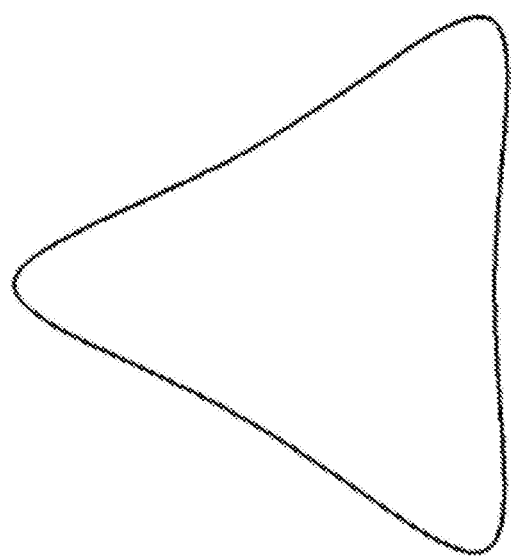
Figure 38:
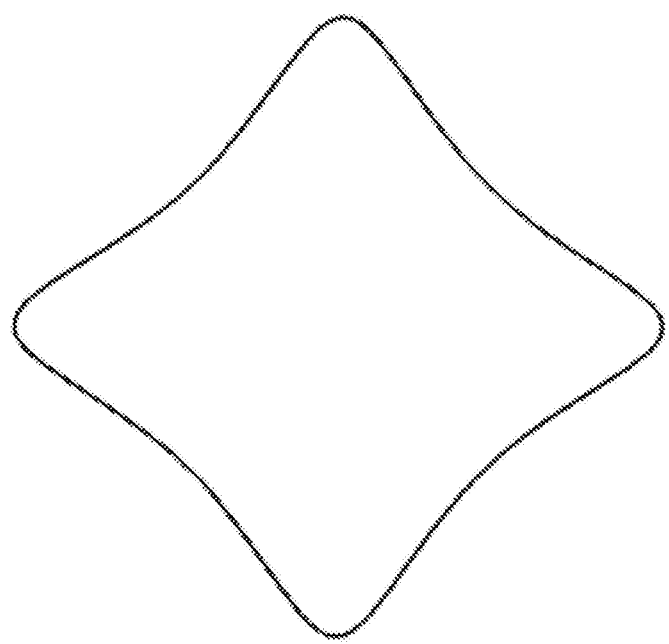

If, based on the ellipse or another specific case of an oval (for example three primary and secondary directions) which has the same number of primary and secondary directions with which a positive and non-positive fit can be obtained, it is desired to reduce the number of positioning options which result in a positive and non-positive fit, this can be achieved by changing the origin of at least one primary or secondary direction, increasing or reducing the length of at least one primary or secondary direction (FIG. 7, FIG. 8 and FIG. 27 and FIG. 28), or by changing the angle of at least one primary or secondary direction relative to the two adjacent primary or secondary directions (FIG. 29 and FIG. 30). A different number of primary and secondary directions of at least one different length would have the same effect. Furthermore, this can be achieved if the change of curvature differs between the individual primary and/or secondary directions in accordance with φ, or differs non-uniformly. With a suitable number of primary and secondary directions and with the corresponding lengths, a single or multiple number of positioning options can be produced which need not correspond to the number of primary and secondary directions, but still has a positive and non-positive fit. However, it should be noted in this instance that with one positioning option which does not have a positive fit, there is a risk when fixing the structural part to the post part, for example with a screw, that either the structural part or the post part will be damaged. This could lead to the post part having to be removed from the patient's jaw.

The following formulae are used as a basis to derive the formula for calculating the height of lift ΔH as a function of the angle of rotation ω.

The linear eccentricity e of an ellipse (FIG. 3) is defined by:

$$e = \sqrt{R^2 - r^2}$$

The numerical eccentricity ε can be calculated from the linear eccentricity by the following formula $$\varepsilon = \frac{e}{R}$$

In order to calculate the varying radius $\Delta r_{(\phi)}$ the angle φ (FIG. 3) is inserted and the values thereof must be input into the radian measure. φ[°] is converted into φ[radian measure] by the following formula:

$$\varphi = \varphi * \frac{\pi}{180°}$$

The ellipse equation $\Delta r_{(\phi)}$ (polar coordinates) is given by the following equation:

$$\Delta R(\varphi) = \frac{r}{\sqrt{1 - \varepsilon^2 * \cos^2(\varphi)}}$$

Figure 41:
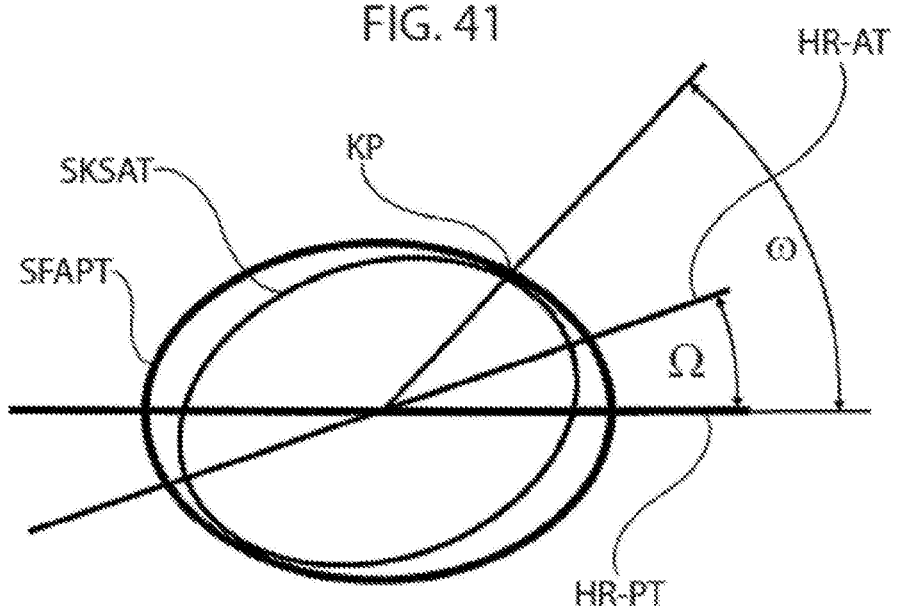
FIG. 41 is a schematic view of an ellipse.
Figure 42:
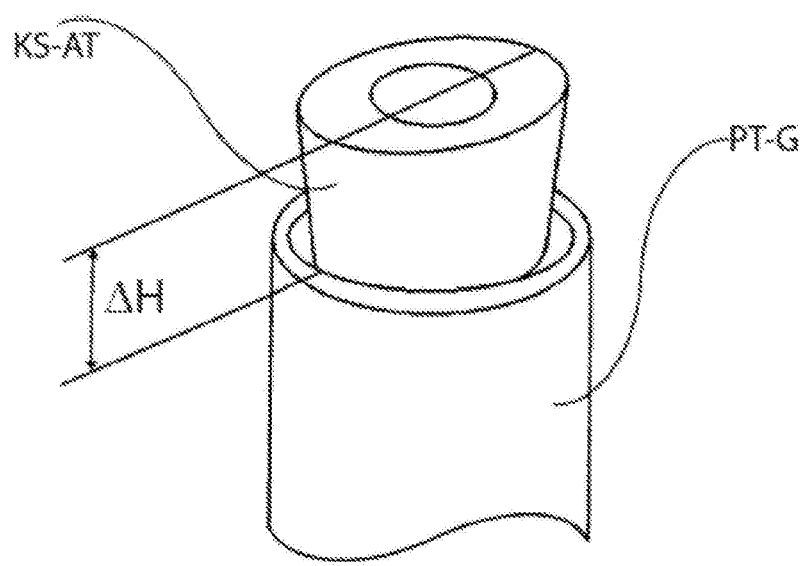
FIG. 42 shows a contact pin inserted into a shaped recess.

If the contact pin (which is elliptical and conical in this example) integrally moulded on the structural part is inserted into the shaped recess in the post part, which shaped recess is also elliptical and conical and the geometry of which is adapted to the contact pin, this can only result in a positive fit and planar contact between the elliptical and conical surfaces if the primary directions of the contact pin and the primary directions of the shaped recess are parallel (and therefore the secondary directions of the contact pin are also parallel to the secondary directions of the shaped recess) and the shafts of the contact pin and of the shaped recess are orientated axially to one another. In this case the contact pin can penetrate furthest into the shaped recess and planar contact between the two components can be achieved. If the axial orientation remains, however, the primary and secondary directions of the contact pin are rotated relative to the primary and secondary directions of the shaped recess, giving the angle Ω (FIG. 41). With the exact same cone angles of the contact pin and of the shaped recess, two linear contacts are produced between the contact pin and the shaped recess. If, as a result of production, there is a small difference in the cone angles, two contact points are produced or else one contact point and one contact line. In any case, when Ω≠0 the contact pin no longer penetrates so deeply into the shaped recess as when Ω=0. The difference between the maximum depth of penetration when Ω=0 and the actual depth of penetration when Ω≠0 or Ω>0 and Ω≤90° gives the height of lift ΔH. The maximum height of lift ΔH is given in the case of an ellipse with an angle of rotation of Ω=90°.

With other geometries comprising more than two primary and secondary directions, with the same number of primary and secondary axes arranged at the same angle to one another, a maximum height of lift ΔH is given with $$\Omega = \frac{360°}{2 * \lambda}$$

where λ= number of primary directions or number of secondary directions.

It can be clearly seen in FIG. 41 that with an elliptical geometry the angle of rotation Ω between the primary directions of the contact pin and of the shaped recess is not the same angle as the contact angle ω between the primary direction of the shaped recess and the contact point of the contact pin and of the post part. Only when the angle of rotation Ω=90° is an angle of 90° also given for ω.

The height of lift ΔH as a function of the contact angle w can be calculated as follows.

ω[°] is converted into w[radian measure] by the following formula:

$$\omega = \omega * \frac{\pi}{180°}$$

The difference between R and the radius $\Delta r_{(\phi)}$ produced at the point of contact between the contact pin and the shaped recess is decisive for the height of lift ΔH. This difference in radius ψ is described by the following formula.

$$\Delta r_{(\omega)} = \frac{d}{\sqrt{1 - \varepsilon^2 * \cos^2(\omega)}}$$

$$\psi = Do - \Delta r_{(\omega)}$$

The height of lift ΔH can be calculated by the following formula using the difference in radius ψ and the cone angle β of the contact or of the shaped recess (FIG. 4).

$$\Delta H = \frac{\psi}{\tan(\beta)}$$

Figure 44:
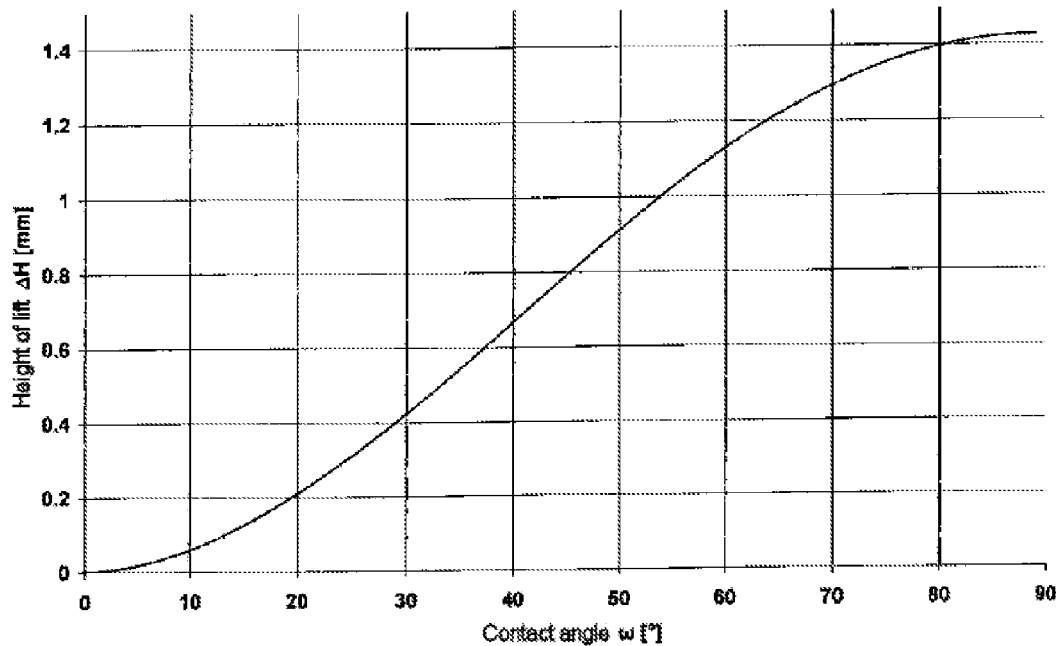
FIG. 44 is a graphical illustration of the curve profile of the height of lift (ΔH) of a structural part as a function of the contact angle(ω).

In the graph of FIG. 44 the curve profile of the height of lift ΔH is illustrated as a function of the contact angle ω=)(0°–90° and of the parameters Do=3.1 mm, do =2.8 mm and cone angle β=6°.

Owing to the combination of a short contact point between the post part and the structural part, in the form of an oval and conical contact pin, in the form of a male mould, integrally moulded onto the structural part and a correspondingly moulded shaped recess in the post part, further advantages are provided which are decisive for the clinical application. A connection formed in this manner combines a tight coupling point, high rotational strength and high strength under axial and extra-axial forces, torque and bending moments with a very short overall height and without any changes, apart from the conical inclination, in shape or external form over the length of the common contact point between the post part and structural part.

A decisive advantage is afforded over conventional cone connections, in particular in the case of the impression. Conventional cone connections have, starting from the upper region of the post part in an apical direction, first the conical region for sealing, transferring the axial and extra-axial forces and inhibiting the torques about the axis of the post part. The rotation locking mechanism is often additionally attached therebeneath and also serves as an indexing for the transfer of the rotatory orientation of the post part. If, with such a post part, an impression is to be made including the rotatory orientation, it is necessary to detect the rotatory orientation very deeply in the post part. This hinders the impression in the case of post parts in the patient's mouth which are angled too sharply to one another. With impression technology the impression posts are removed, including the impression material. The shorter the depth to which the impression posts engage in the post part, the simpler is the removal of the impression, including the impression posts. This affords the advantage, with a conical sealing face including the indexing, that the impression posts have to engage in the post part up to a depth less than 2 mm, advantageously less than 1.5 mm and in a particularly favourable variant less than 1 mm.

In order to improve the rotatory orientation of the structural part relative to the post part it is expedient to modify the surface properties of the contact points. In this instance the focus is on reducing sliding friction. It is advantageous to modify at least one surface, two surfaces in a favourable variant, and all three of the following surfaces in an optimum variant. These surfaces are the contact surface between the post part and the structural part (on the post part side and on the structural part side) and the seat of the connecting screw in the structural part. The following methods have demonstrated a positive effect: polishing, anodising, type II anodising, titanium nitride coating, and coating with monocrystalline and/ or polycrystalline carbon or diamond.

LIST OF REFERENCE NUMERALS 1 dental implant
2 post part
4 structural part
6 thread
8 contact pin
10 shaped recess
12 connecting screw
14 outer thread
16 inner thread
18 screw head
20, 22 arrow
D maximum diameter
d minimum diameter
h cone length of the contact pin on the structural part
$\Delta H$ height of lift of the structural part by rotation in the post part about the angle $\omega$
D maximum diameter
d minimum diameter
Da maximum apical diameter
da minimum apical diameter
Do maximum occlusal diameter
do minimum occlusal diameter
R maximum radius
r minimum radius
$\Delta r$ variable radius and dependency of the angle $\phi$ (for example with an ellipse)
HR primary direction
NR secondary direction
HR-1-HR-6 primary direction 1 to primary direction 6
NR-1-NR-6 secondary direction 1 to secondary direction 6
$\theta$ angle between a primary and secondary direction
$\theta 1$-$\theta 3$ angle between a primary and a secondary direction 1-3
HRL length of the primary direction
NRL length of the secondary direction
HRL-1-HRL-2 length of primary direction 1 and length of primary direction 6
NRL-1-NRL-2 length of secondary direction 1 and length of secondary direction 6
$\Phi$ angle between a primary direction or primary direction and the variable radius r, for example with an ellipse
$\omega$ rotational offset angle between the structural part and the post part
$\beta$ cone angle of the contact pin integrally moulded on the structural part or cone angle of the shaped recess formed in the post part
$\Omega$ angle of rotation between the primary directions of the elliptical, conical contact pin and the elliptical, conical primary direction of the shaped recess
$\omega$ angle between a primary direction of the shaped recess and the contact produced with an angle of rotation $\Omega$ between the contact pin and the shaped recess
SKSAT sectional geometry of an elliptical contact pin of a structural part
SFAPT sectional geometry of an elliptical shaped recess in the post part
KP contact point
HR-AT primary direction of the structural part
HR-PT primary direction of the post part
KS-AT contact pin of a structural part
PT-G post part without outer thread
X x-axis
Y y-axis
$F_1$-$F_2$ fixed points 1 and 2
$P_{(x, y)}$ point/points formed by x and y coordinates
$S_1$-$S_2$ distance between $F_1$ and $P_{(x, y)}$ or distance between $F_1$ and $P_{(x, y)}$

The invention claimed is:

1. A dental implant comprising
a post part which can be placed in a jaw bone, and a structural part associated with said post part, to which structural part a denture piece can be attached,
the structural part comprising an integrally moulded contact pin which can be placed in an associated shaped recess in the post part with a positive fit,
wherein the cross-section of the contact pin integrally moulded on the structural part and the cross-section of the shaped recess in the post part have at least one primary direction in which the radius of the cross-section adopts a relative maximum value R0, and at least one secondary direction in which the radius of the cross-section adopts a relative minimum value,
wherein the outer contours of the cross-sections of the contact pin and the shaped recess are selected in such a way that they have precisely one tangent at each point, and wherein both the contact pin of the structural part and the shaped recess in the post part are tapered, wherein the structural part when placed in the post part has a lift height ΔH, as a function of a taper angle β and the minimum radius r of said at least one secondary direction, as follows:

$$\Delta H = \frac{R0 - r}{\tan(\beta)},$$

and wherein the lift height ΔH, as a function of a rotational offset from a rotation between the structural part and the post part from a starting position in which said at least one primary direction of the contact pin is rotationally aligned with said at least one primary direction of said shaped recess to an end position in which said at least one primary direction of said contact pin is rotationally aligned with said at least one secondary direction of said recess, is at least 900 μm/n, where n is the number of primary directions of the structural part in the post part, and wherein the lift height prevents outer threads of a connecting screw inserted in the structural part from engaging inner threads of the post part until the rotational offset of the contact pin and shaped recess is such that a force applied by the connecting screw on the structural part begins to self-center the structural part in the post part.

2. The dental implant according to claim 1, wherein the outer threads of the connecting screw do not engage the inner threads of the post part where the rotational offset between the structural part and the post part is 360°/(2×n) where n is the number of primary directions of the structural part in the post part.

3. The dental implant according to claim 1, wherein upon self-centering and upon tightening of the connecting screw, the outer threads of the connecting screw and the inner threads of the post part become engaged.

4. The dental implant of claim 1, wherein
the post part has at least three primary directions in which the radius of the cross-section adopts a relative maximum value, and at least three secondary directions in which the radius of the cross-section adopts a relative minimum value.

5. The dental implant according to claim 1, in which both the contact pin of the structural part and the shaped recess in the post part have the taper angle in the range of 1° to 15°.

6. The dental implant according to claim 1, in which both the contact pin of the structural part and the shaped recess in the post part have the taper angle in the range of between 5° and 10°.

7. The dental implant according to claim 1, in which both the contact pin of the structural part and the shaped recess in the post part have the taper angle of approximately 6°.

8. The dental implant according to claim 1, in which the contact pin and the shaped recess each comprise at least one segment along their respective lengths that includes both the cross-section having the primary and secondary directions and a conical shape.

9. The dental implant according to claim 1, in which the outer contours of the cross-sections are selected in such a way that they are intersected at most at two points by any straight lines.

10. The dental implant according to claim 1, in which the outer contours of the cross sections are selected in such a way that they correspond to a segment of an oval in regions between each of two primary directions.

11. The dental implant according to claim 1, in which the contact pin integrally moulded on the structural part and the shaped recess, associated with said contact pin, in the post part each have a tri-oval cross-section.

12. The dental implant according to claim 1, wherein tightening of the connecting screw results in the contact pin having the positive fit with the shaped recess.

13. The dental implant according to claim 1, in which the contours of the cross sections are each selected in such a way that for n being the number of primary directions, the ratio of minimum value to maximum value of the radius is in the interval is as follows:

| Number n of primary directions | Ratio minimum radius/maximum radius |
|---|---|
| 3 | 70-95% |
| 4 | 80-97% |
| 5 | 90-98% |
| 6 | 95-99% |
| 7 | 96-99% |
| 8 | 97-99% |
| 9 | 98-99%. |

* * * * *